United States Patent
Zhao et al.

(10) Patent No.: US 10,232,037 B2
(45) Date of Patent: Mar. 19, 2019

(54) SUPRAMOLECULAR HYDROGEL OF FMLF-BASED MOLECULES AND USE THEREOF

(71) Applicants: BRANDEIS UNIVERSITY, Waltham, MA (US); CHILDREN'S MEDICAL CENTER CORPORATION, Boston, MA (US)

(72) Inventors: Fan Zhao, Waltham, MA (US); Jingyu Li, Boston, MA (US); Hongbo R. Luo, Boston, MA (US); Bing Xu, Waltham, MA (US)

(73) Assignees: Brandeis University, Waltham, MA (US); Children's Medical Center Corporation, Boston, MA (US)

(*) Notice: Subject to any disclaimer, the term of this patent is extended or adjusted under 35 U.S.C. 154(b) by 0 days.

(21) Appl. No.: 15/115,385

(22) PCT Filed: May 29, 2014

(86) PCT No.: PCT/US2014/039969
§ 371 (c)(1),
(2) Date: Jul. 29, 2016

(87) PCT Pub. No.: WO2015/116242
PCT Pub. Date: Aug. 6, 2015

(65) Prior Publication Data
US 2017/0007696 A1   Jan. 12, 2017

(51) Int. Cl.
| | |
|---|---|
| A61K 39/00 | (2006.01) |
| A61K 39/02 | (2006.01) |
| A61K 49/00 | (2006.01) |
| A61K 39/39 | (2006.01) |
| A01N 37/46 | (2006.01) |
| A61K 45/06 | (2006.01) |
| C07K 14/00 | (2006.01) |
| A61K 9/00 | (2006.01) |
| A61K 9/06 | (2006.01) |
| A61K 38/06 | (2006.01) |
| A61K 38/07 | (2006.01) |
| A61K 38/08 | (2019.01) |
| A61K 38/10 | (2006.01) |
| A61K 38/16 | (2006.01) |
| C07K 5/08 | (2006.01) |
| C07K 5/10 | (2006.01) |
| C07K 7/06 | (2006.01) |
| C07K 7/08 | (2006.01) |
| A61K 38/00 | (2006.01) |

(52) U.S. Cl.
CPC .............. *A61K 39/39* (2013.01); *A01N 37/46* (2013.01); *A61K 9/0019* (2013.01); *A61K 9/06* (2013.01); *A61K 38/06* (2013.01); *A61K 38/07* (2013.01); *A61K 38/08* (2013.01); *A61K 38/10* (2013.01); *A61K 38/16* (2013.01); *A61K 45/06* (2013.01); *C07K 5/0802* (2013.01); *C07K 5/1002* (2013.01); *C07K 7/06* (2013.01); *C07K 7/08* (2013.01); *C07K 14/00* (2013.01); *C07K 14/001* (2013.01); *A61K 38/00* (2013.01); *A61K 2039/55516* (2013.01); *A61K 2039/572* (2013.01); *A61K 2039/575* (2013.01); *C07K 2319/00* (2013.01)

(58) Field of Classification Search
CPC ................................ A61K 38/00; A61K 38/03
USPC .................. 424/9.1, 9.2, 184.1, 185.1, 234.1
See application file for complete search history.

(56) References Cited

U.S. PATENT DOCUMENTS

| | | |
|---|---|---|
| 7,893,056 B2 | 2/2011 | Qin et al. |
| 2012/0142616 A1 | 6/2012 | Gao et al. |
| 2014/0148410 A1 | 5/2014 | Xu |

FOREIGN PATENT DOCUMENTS

| | | |
|---|---|---|
| WO | 2010/151644 A2 | 12/2010 |
| WO | 2012/166705 A2 | 12/2012 |
| WO | 2012/166706 A2 | 12/2012 |
| WO | 2014/138367 A1 | 9/2014 |

OTHER PUBLICATIONS

Brockhause, I., et al., (Essentials of Glycobiology, 2:1-11, 2009).*
Orbach, R., et al. (Biomacromolecules, 10:2646-2651, 2009).*
Ye, R.D., et al. (Pharmacological Reviews, 61(2); 119-161, 2009).*
Wang, J., et al. (Colloids and Surfaces B: Biointerfaces, 80:155-160, 2010).*
Liang, G., et al. (Langmuir, 25(15):8419-8422, 2009).*
Brockhausen et al., "O-Gal N-acetylgalactosamine Glycans," Essentials of Glycobiology 2:1-11 (2009).
Ikeda et al., "Three-Dimensional Encapsulation of Live Cells by Using a Hybrid Matrix of Nanoparticles in a Supramolecular Hydrogel," Chemistry A European Journal 14:10808-10815 (2008).
Liang et al., "Supramolecular Hydrogel of a D-Amino Acid Dipeptide for Controlled Drug Release in Vivo," Langmuir 25(15):8419-8422 (2009).
Orbach et al., "Self-Assembled Fmoc-Peptides as a Platform for the Formation of Nanostructures and Hydrogels," Biomacromolecules 10:2646-2651 (2-009).
Southgate et al., "Identification of Formyl Peptides from S. aureus and L. monocytogenes as Highly Potent Chemoattractants for Mouse Neutrophils," The FASEB Journal 22:1-2 (2008) abstract.
Wang et al., "A Saccharide-based Supramolecular Hydrogel for Cell Culture," Carbohydrate Research 346:1013-1017 (2011).
Wang et al., "A Hybrid Hydrogel for Efficient Removal of Methyl Violet from Aqueous Solutions," Colloids and Surfaces B: Biointerfaces 80:155-160 (2010).
Ye et al., "International Union of Basic and Clinical Pharmacology. LXXIII. Nomenclature for the Formyl Peptide Receptor (FPR) Family," Pharmacological Reviews 61:119-161 (2009).
Gao et al., "Imaging Enzyme-Triggered Self-Assembly of Small Molecules Inside Live Cells," Nat Commun. 3:1033 (2012).

(Continued)

*Primary Examiner* — Rodney P Swartz
(74) *Attorney, Agent, or Firm* — LeClairRyan PLLC

(57) ABSTRACT

The invention relates to the application of peptides that can self-assemble to form supramolecular nanofibrils and hydrogels, hydrogel compositions containing the self-assembled supramolecular nanofibrils, and methods of uses and making the hydrogel compositions.

20 Claims, 9 Drawing Sheets
Specification includes a Sequence Listing.

(56) References Cited

OTHER PUBLICATIONS

Li et al., "Molecular Nanofibers of Olsalazine Confer Supramolecular Hydrogels for Reductive Release of an Anti-Inflammatory Agent," J Am Chem Soc. 132(50):17707-709 (2010).
Zhang et al., "Versatile Small Molecule Motifs for Self-Assembly in Water and Formation of Biofunctional Supramolecular Hydrogels," Langmuir. 27(2):529-37 (2011).
Li et al., "The Conjugation of Nonsteroidal Anti-Inflammatory Drugs (NSAID) to Small Peptides for Generating Multifunctional Supramolecular Nanofibers/Hydrogels," Beilstein J. Org. Chem. 9:908-917 (2013).
Li et al., "Introducing D-Amino Acid or Simple Glycoside into Small Peptides to Enable Supramolecular Hydrogelators to Resist Proteolysis," Langmuir. 28(37):13512-517 (2012).
Li et al., "'Molecular Trinity' for Soft Nanomaterials: Integrating Nucleobases, Amino Acids, and Glycosides to Construct Multifunctional Hydrogelators," Soft Matter. 8(10):2801-806 (2012).
Zhao et al., "A Novel Anisotropic Supramolecular Hydrogel with High Stability over a Wide PH Range," Langmuir. 27(4):1510-12 (2011).
Li et al., "Supramolecular Nanofibers and Hydrogels of Nucleopeptides," Angew Chem Int Ed Engl. 50(40):9365-69 (2011).
PCT International Search Report and Written Opinion for corresponding PCT/US2014/039969, filed May 29, 2014 (dated Oct. 6, 2014).

\* cited by examiner

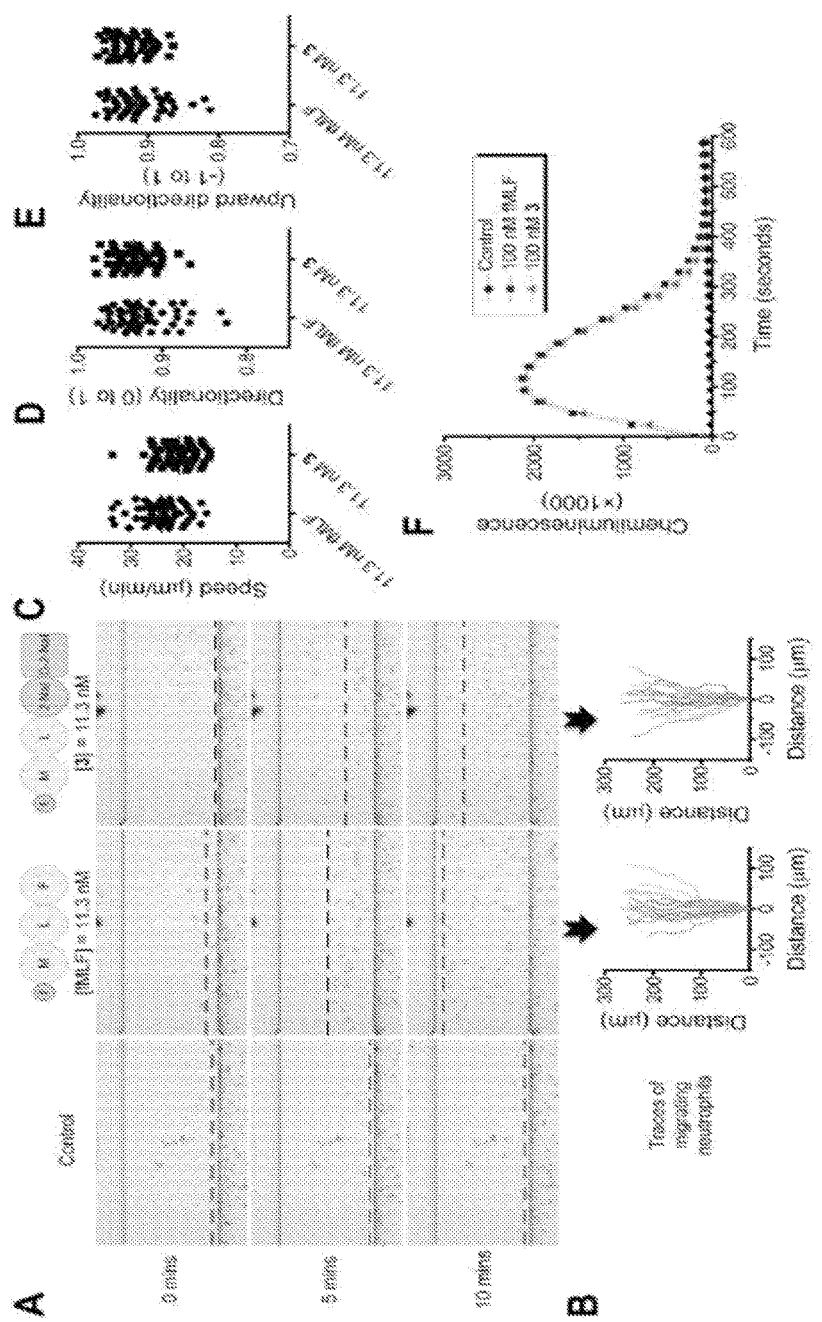
FIGS. 6A-F

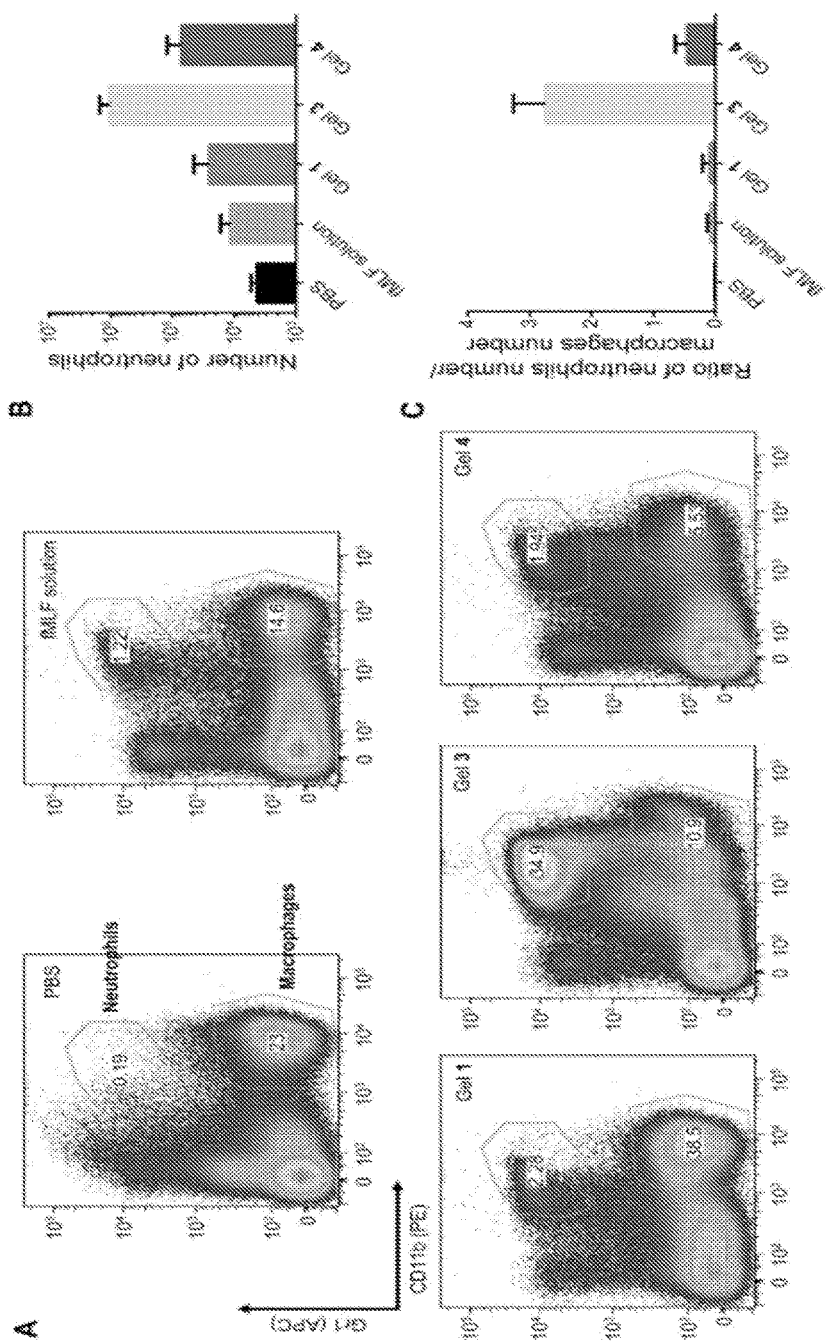
FIGS. 7A-C

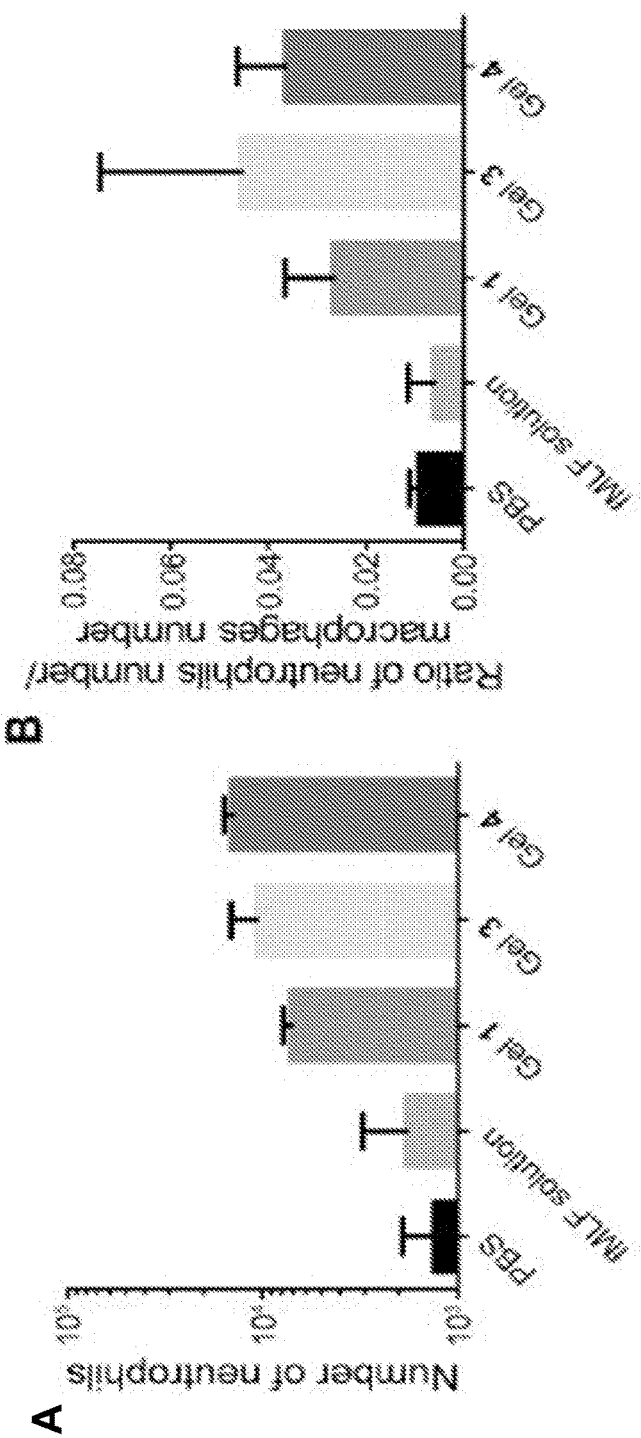
FIGS. 8A-B

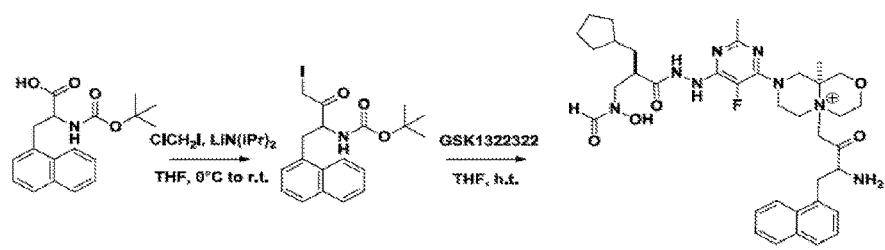
GSK1322322-(2-Nal_D) Peptide 2
FIG. 9A
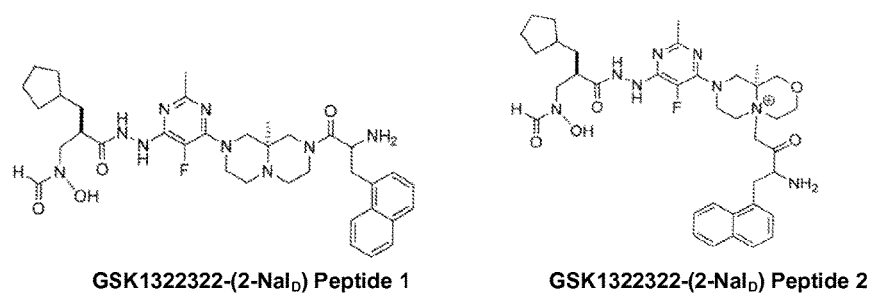
GSK1322322-(2-Nal_D) Peptide 1        GSK1322322-(2-Nal_D) Peptide 2
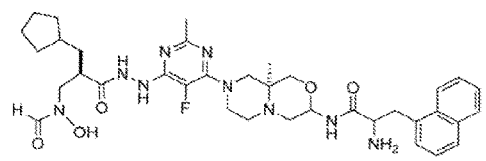
GSK1322322-(2-Nal_D) Peptide 3
FIG. 9B

SUPRAMOLECULAR HYDROGEL OF FMLF-BASED MOLECULES AND USE THEREOF

This invention was made with government support under R01 CA142746, R01 HL085100, R01 HL092020, R01 AI076471, and R01 GM076084 awarded by the National Institutes of Health. The government has certain rights in the invention.

This application is a national stage application under 35 U.S.C. § 371 of PCT Application No. PCT/US2014/039969, filed May 29, 2014, which claims the priority benefit of U.S. Provisional Patent Application No. 61/935,190, filed Feb. 3, 2014, which is hereby incorporated by reference in its entirety.

FIELD OF THE INVENTION

This invention relates to the application of peptides that can self-assemble to form supramolecular nanofibrils and hydrogels, hydrogel compositions containing the self-assembled supramolecular nanofibrils, and methods of using and making the hydrogel compositions.

BACKGROUND OF THE INVENTION

Upon the breaching of the host physical barrier by intruding microorganisms, neutrophils, among all the leukocytes, are the first to influx into a focus of bacterial invasion for host defense (Kolaczkowska et al., *Nat. Rev. Immunol.*, 13, 159-175 (2013)). Neutrophils used to be considered to function exclusively as the effector cells in the innate phase of the immune response. However, the old view was challenged since a growing body of evidence that neutrophils play a crucial role in framing immune response, both innate and adaptive immunity (Nathan, *Nat. Rev. Immunol.*, 6, 173-182 (2006); Mantovani et al., *Nat. Rev. Immunol.*, 11, 519-531 (2011)). For example, neutrophils are found to have a B cell-helper neutrophil population in the splenic marginal zone and these neutrophils can activate marginal zone B cells to secrete immunoglobulins against T cell-independent antigens (Puga et al. *Nat. Immunol.*, 13, 170-180 (2012)).

The efficient recruitment of neutrophils depends on many signals, including N-formyl peptides, chemokines, complements and leukotrienes (Kolaczkowska et al., *Nat. Rev. Immunol.*, 13, 159-175 (2013)). As the by-products of the protein translation in the invading bacteria, N-formyl peptides form molecular gradients originating from the bacteria in the infected tissue. And the gradients of N-formyl peptides signal neutrophils to migrate (i.e., chemotaxis) towards their targets while overriding other minor signals, such as IL-8 and MIP-2 (Kolaczkowska et al., *Nat. Rev. Immunol.*, 13, 159-175 (2013)). Proposed in 1965 and confirmed in 1984, N-formyl-L-methionyl-L-leucyl-L-phenylalanine (fMLF) represents the best-known N-formyl peptide and one of the most well-established chemoattractants for neutrophils (Ye et al., *Pharmacol. Rev.*, 61, 119-161 (2009)).

Recognized for its potential as a useful reagent to induce acute inflammation in vivo, fMLF, in the form of aqueous solution, has been injected subcutaneously (Gao et al., *J. Exp. Med.*, 189, 657-662 (1999)), intravenously (Jagels et al., *Blood*, 85, 2900-2909 (1995)), intraplantarly (Rittner et al., *PLoS Pathog.*, 5, e1000362 (2009)), intradermally (Feng et al., *J. Exp. Med.*, 187, 903-915 (1998)) or just topically applied on the microvasculature (Oda et al., *J. Leukoc. Biol.*, 52, 337-342 (1992)) to study the biology of neutrophils for various applications. Although the aqueous solution of fMLF is able to induce the accumulation of neutrophils, its effect is relatively weak and transient (2-6 hr) (Colditz et al., *J. Immunol.*, 133, 2169-2173 (1984)).

Demonstrated in a recent work, the intratumoral injection of fMLF solution every two days after the inoculation of tumor cells slows down the tumor growth in a xenograft tumor model (Zhang et al., *Lab. Invest.*, 76, 579-590 (1997)). Similarly, the daily intratumoral injection of another chemoattractant, chemerin, decreases the tumor growth (Pachynski et al., *J. Exp. Med.*, 209, 1427-1435 (2012)). To maintain a meaningful local concentration of the chemoattractants, both studies required frequent intratumoral injections (Zhang et al., *Lab. Invest.*, 76, 579-590 (1997); Pachynski et al., *J. Exp. Med.*, 209, 1427-1435 (2012)).

A formulation of chemoattractant (e.g., fMLF) for prolonged release, not only acts as a useful tool to study the biology of neutrophils over long duration, but also holds promises for therapeutic applications, like cancer treatment. This potential has already led to explorations of different formulations of fMLF (Gauthier et al., *Infect. Immun.*, 75, 5361-5367 (2007); Kress et al., *Nat. Meth.*, 6, 905-909 (2009); Zhao et al., *Biomaterials*, 26, 5048-5063 (2005)), such as particles of fMLF in suspensions produced by sonication for studying neutrophil infiltration into pulmonary alveoli during murine pneumococcal pneumonia (Gauthier et al., *Infect. Immun.*, 75, 5361-5367 (2007)), physically encapsulated N-formyl peptides in poly(lactic-co-glycolic acid) (PLGA) microbeads for inducing chemotaxis of neutrophils (Kress et al., *Nat. Meth.*, 6, 905-909 (2009)), or human monocytes and monocyte-derived dendritic cells (DCs) (Zhao et al., *Biomaterials*, 26, 5048-5063 (2005)) in vitro.

Despite this progress, heterogeneous suspensions of fMLF particles are far from ideal for in vivo applications, and physical encapsulation using polymeric materials suffers from several limitations including burst release, low capacity for payload, and slow bioresorption of the polymeric materials. These limitations demand the development of new approaches to attract neutrophils in vivo.

The present invention overcomes these and other deficiencies in the art.

SUMMARY OF THE INVENTION

A first aspect of the invention relates to a formyl peptide receptor agonist peptide that is capable of self-assembly to form a hydrogel. One peptide according to this aspect of the invention includes up to about 35 amino acids, and has a formylated or acetylated N-terminal residue and a C-terminal residue selected from the group of 2-Nal or 2-Nal$_D$.

A second aspect of the invention relates to an immunogenic conjugate that includes an antigenic peptide conjugated to the peptide according to the first aspect of the invention.

A third aspect of the invention relates to a hydrogel composition that includes an aqueous medium and a peptide according to the first aspect of the invention, wherein the peptide self assembles to form nanofibrils.

A fourth aspect of the invention relates to a method for eliciting a prolonged inflammatory response in a subject. This method includes administering to a subject in need thereof a therapeutically effective amount of the hydrogel composition according to the third aspect of the invention.

A fifth aspect of the invention relates to a method for inducing prolonged neutrophil accumulation in vivo. This method includes administering to a subject in need thereof a therapeutically effective amount of the hydrogel composition according to the third aspect of the invention, wherein said administering is effective to release the formyl or acetyl peptide over a period of time exceeding from about 12 hours, thereby inducing prolonged neutrophil accumulation at the site of administration.

A sixth aspect of the invention relates to a method for treating a cancerous condition. This method includes administering to a subject having a cancerous condition a therapeutically effective amount of the hydrogel composition according to the third aspect of the invention, wherein said administering is effective to inhibit tumor growth or shrink tumor size.

A seventh aspect of the invention relates to a method of treating a bacterial infection. This method includes administering to a patient having a bacterial infection a therapeutically effective amount of the hydrogel composition according to the third aspect of the invention, wherein said administering is effective to treat the bacterial infection. This may include treatment for sepsis.

An eighth aspect of the invention relates to a method of making a hydrogel composition. This method includes introducing a peptide according to the first aspect of the invention into an aqueous medium, wherein the peptide self-assembles for form nanofibrils.

A ninth aspect of the invention relates to a formyl peptide receptor antagonist peptide that is capable of self-assembly to form a hydrogel. A peptide according to this aspect of the invention includes up to about 35 amino acids and has a tert-butyloxycarbonylated (t-Boc) or ureido N-terminal residue and a C-terminal residue selected from the group of 2-Nal or 2-Nal$_D$.

A tenth aspect of the invention relates to a hydrogel composition that includes an aqueous medium and a peptide according to the ninth aspect of the invention, wherein the peptide self assembles to form nanofibrils.

An eleventh aspect of the invention relates to a method for decreasing neutrophil toxicity at an inflammation site in a subject. This method includes administering to a subject in need thereof a therapeutically effective amount of the hydrogel composition according to the tenth aspect of the invention.

A twelfth aspect of the invention relates to a method for inhibiting neutrophil accumulation in vivo. This method includes administering to a subject in need thereof a therapeutically effective amount of the hydrogel composition according to the tenth aspect of the invention, wherein said administering is effective to release the peptide over a period of time exceeding about 12 hours, thereby inhibiting prolonged neutrophil accumulation at the site of administration.

A thirteenth aspect of the invention relates to a method for inhibiting chemotactic migration of neutrophils in vivo. This method includes administering to a subject in need thereof a therapeutically effective amount of the hydrogel composition according to the tenth aspect of the invention.

A fourteenth aspect of the invention relates to a method of making a hydrogel composition. This method includes introducing a peptide according to the ninth aspect of the invention into an aqueous medium, wherein the peptide self-assembles to form nanofibrils.

A fifteenth aspect of the invention relates to a peptide or peptidomimetic that includes a deformylase inhibitor component and is capable of self-assembly to form a hydrogel. A peptide according to this aspect of the invention includes up to about 35 amino acids, the peptide or peptidomimetic having an N-terminal deformylase inhibitor component and C-terminal amino acid residue selected from the group of 2-Nal or 2-Nal$_D$.

A sixteenth aspect of the invention relates to a hydrogel composition that includes an aqueous medium and a peptide or peptidomimetic according to the fifteenth aspect of the invention, wherein the peptide or peptidomimetic self assembles to form nanofibrils.

A seventeenth aspect of the invention relates to a method of treating a bacterial infection that includes administering to a patient having a bacterial infection a therapeutically effective amount of the hydrogel composition according to the sixteenth aspect of the invention, wherein said administering is effective to treat the bacterial infection.

Most of immunomodulatory materials (e.g., vaccine adjuvants such as alum) modulate adaptive immunity (Hubbell et al., *Nature*, 462, 449-460 (2009); Ali et al., *Nat. Mater.*, 8, 151-158 (2009); St. John et al., *Nat. Mater.*, 11, 250257 (2012); DeMuth et al., *Nat. Mater.*, 12, 367-376 (2013), each of which is hereby incorporated by reference in its entirety), and yet little effort has focused on developing materials to regulate innate immunity. Traditionally considered as short-lived effector cells from innate immunity primarily for the clearance of invading microorganisms without specificity, neutrophils exhibit key role in launching and shaping the immune response (Nathan, *Nat. Rev. Immunol.*, 6, 173-182 (2006); Mantovani et al., *Nat. Rev. Immunol.*, 11, 519-531 (2011), each of which is hereby incorporated by reference in its entirety). As described herein, the incorporation of unnatural amino acids into a well-known chemoattractant, N-formyl-L-methionyl-L-leucyl-L-phenylalanine (fMLF) (Ye et al., *Pharmacol. Rev.*, 61, 119-161 (2009), which is hereby incorporated by reference in its entirety) offers a facile approach to create a de novo, multifunctional chemoattractant that self-assembles to form supramolecular nanofibrils and hydrogels (Estroff et al., *Chem. Rev.*, 104, 1201-1218 (2004), which is hereby incorporated by reference in its entirety). This de novo chemoattractant exhibits not only cross-species chemoattractant activity to human and murine neutrophils, but also effectively resists proteolysis. Thus, its hydrogel, in vivo, self-releases the chemoattractant (monomers) and attracts neutrophils to the desired location in a sustainable manner. The hydrogels can also act as the depot for inducing prolonged neutrophil accumulation in murine peritonitis model. As a novel and general approach to generate a new class of biomaterials for modulating innate immunity, the invention offers an unprecedented, prolonged acute inflammation model for developing various new applications.

Additional aspects, advantages and features of the invention are set forth in this specification, and in part will become apparent to those skilled in the art on examination of the following, or may learned by practice of the invention. The inventions disclosed in this application are not limited to any particular set of or combination of aspects, advantages and features. It is contemplated that various combinations of the stated aspects, advantages and features make up the inventions disclosed in this application.

BRIEF DESCRIPTION OF THE DRAWINGS

FIGS. 6A-F show the induction of chemotaxis and reactive oxygen species (ROS) production of human neutrophils by f-MLF peptide and f-MLF-based hydrogelator 3 in vitro.

FIGS. 7A-C illustrate how hydrogelators 1, 3 and 4 prolonged the accumulation of murine neutrophils in vivo as compared to f-MLF peptide.

FIGS. 8A-B shows the number of neutrophils (8A) and the ratio of the number of neutrophils versus the number of macrophages (8B) from the FACS quantification of the cells collected from the peritoneal lavage of wild-type mice 48 hours after receiving intraperitoneal injections of 500 μl of PBS (control), the solution of fMLF peptide, and the hydrogelators 1, 3 and 4 containing 0.935 μmole of peptides.

FIG. 9A shows a synthesis scheme for preparing a GSK13233322-(D-2-Nal) peptide analog-based hydrogelator and FIG. 9B shows the chemical structures of three GSK13233322-(D-2-Nal) peptide analog-based hydrogelators.

DETAILED DESCRIPTION OF THE INVENTION

Figure 1:
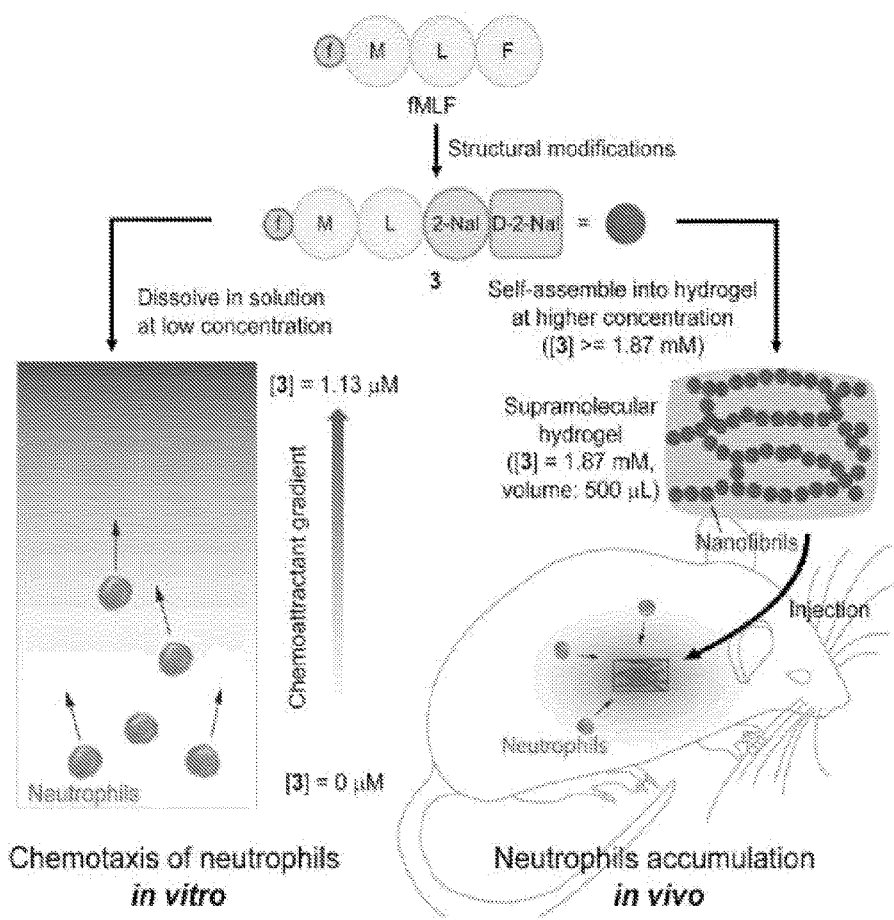
FIG. 1 is an illustration of converting fMLF to fMLF-based hydrogelator 3 to induce chemotaxis of neutrophils in vitro and accumulation of neutrophils in vivo.

One aspect of the invention relates to a formyl peptide receptor agonist peptide that is capable of self-assembly to form a hydrogel. A peptide according to this aspect of the invention includes up to about 35 amino acids, wherein the amino acids include a formylated or acetylated N-terminal residue and a C-terminal residue selected from the group of 2-Nal or 2-Nal$_D$.

The peptide length, as used herein, is up to about 35 amino acids, up to about 30 amino acids, up to about 25 amino acids, up to about 20 amino acids, up to about 15 amino acids, up to about 10 amino acids or between 3 to 10 amino acids. The peptides can include all D-amino acids, all L-amino acids, or a mixture of L-amino acids and D-amino acids. In preferred embodiments, the peptide includes only D-amino acids or a mixture of D-amino acids and L-amino acids where the D-amino acid content is greater than 50%, 60%, 70%, 80%, 90%, or 95%.

The term "amino acid" is intended to embrace all compounds, whether natural or synthetic, which include both an amino functionality and an acid functionality, including amino acid analogues and derivatives. In certain embodiments, the amino acids contemplated in the present invention are those naturally occurring amino acids found in proteins, or the naturally occurring anabolic or catabolic products of such amino acids, which contain amino and carboxyl groups. Amino acids, as used herein, may include both non-naturally and naturally occurring amino acids.

Naturally occurring amino acids are identified throughout by the conventional three-letter and/or one-letter abbreviations, corresponding to the trivial name of the amino acid, in accordance with the following list: Alanine (Ala), Arginine (Arg), Asparagine (Asn), Aspartic acid (Asp), Cysteine (Cys), Glutamic acid (Glu), Glutamine (Gln), Glycine (Gly), Histidine (His), Isoleucine (Ile), Leucine (Leu), Lysine (Lys), Methionine (Met), Phenylalanine (Phe), Proline (Pro), Serine (Ser), Threonine (Thr), Tryptophan (Trp), Tyrosine (Tyr), and Valine (Val). The abbreviations are accepted in the peptide art and are recommended by the IUPAC-IUB commission in biochemical nomenclature.

The term "amino acid" further includes analogues, derivatives, and congeners of any specific amino acid referred to herein, as well as C-terminal or N-terminal protected amino acid derivatives (e.g., modified with an N-terminal or C-terminal protecting group). Furthermore, the term "amino acid" includes both D- and L-amino acids. Hence, an amino acid which is identified herein by its name, three letter or one letter symbol and is not identified specifically as having the D or L configuration, is understood to assume any one of the D or L configurations. For example, 2-Nal or 2-Nal$_D$ refer to the L and D configurations, respectively, of the analogue 3-(2-naphthyl)-alanine.

As used herein the term "peptide" includes native peptides (either degradation products or synthetically synthesized peptides) and further to peptidomimetics, such as peptoids and semipeptoids which are peptide analogs, which may have, for example, modifications rendering the peptides more stable while in a body, having lower immunogenicity and/or higher affinity to their receptors.

As used herein, the term "about" when used in connection with a numerical value denotes an interval of accuracy that is ±10% in certain embodiments, ±5% in other embodiments, ±2.5% in still further embodiments, and ±1% in yet another embodiment.

As used herein and in the appended claims, the singular "a", "an" and "the" include the plural reference unless the context clearly dictates otherwise. Thus, for example, reference to a "peptide" includes a plurality of such peptides.

In one embodiment, the formylated N-terminal residue is f-Met or f-Ala and the C-terminal residue is 2-Nal$_D$.

In another embodiment, the acetylated N-terminal residue is Ac-Ser, Ac-Ala, Ac-Gly, Ac-Thr, Ac-Val, Ac-Cys, or Ac-Lys, and the C-terminal residue is 2-Nal$_D$.

The amino acids residues intermediate the N-terminal and C-terminal residues identified above can be any amino acid, including naturally and non-naturally occurring amino acids. In accordance with one embodiment, amino acids near the C-terminal residue are aromatic. The aromatic side chains cooperate with the C-terminal residue to facilitate self-assembly into fibrils and, hence, gelation. The aromatic amino acids used in the peptides of the present invention include, without limitation, any one or more of phenylalanine, phenylalanine derivatives, tyrosine, tyrosine derivatives, tryptophan, and tryptophan derivatives. Any known or hereinafter developed phenylalanine derivatives, tyrosine derivatives, or tryptophan derivatives can be used in the present invention. Derivatives of these amino acids include the addition of one or more ring substituents.

As a consequence of utilizing entirely D-amino acids or a high proportion of D-amino acids, it is possible to render the peptide protease resistant, e.g., resistant to proteinase K digestion. Presence of the C-terminal 2-Nal$_D$ residue promotes enhanced resistance to proteinase digestion.

The inventive peptides are capable of self-assembling to form hydrogels upon introduction into an aqueous solution and are present in concentrations up to about 10 w/v %, up to about 5 w/v % or between 0.1 and 3 w/v %.

Examples of the peptides according to this aspect of the invention include, without limitation, f-MLF-(2-Nal) (SEQ ID NO: 1), f-MLF-(2-Nal$_D$), f-ML-(2-Nal)-(2-Nal$_D$), f-MIVIL-(2-Nal) (SEQ ID NO: 2), f-MIVIL-(2-Nal$_D$), f-MIFL-(2-Nal) (SEQ ID NO: 3), f-MIFL-(2-Nal$_D$), f-MFINRWLFS-(2-Nal) (SEQ ID NO: 4), f-MFINRWLFS-(2-Nal$_D$), f-MFFINILTL-(2-Nal) (SEQ ID NO: 5), f-MFFINILTL-(2-Nal$_D$), f-AWKYMV$_D$-(2-Nal), f-AWKYMV$_D$-(2-Nal$_D$), f-M$_D$L$_D$F$_D$-(2-Nal$_D$), f-M$_D$L$_D$-(2-Nal$_D$)-(2-Nal$_D$), f-M$_D$I$_D$V$_D$I$_D$L$_D$-(2-Nal$_D$), f-M$_D$I$_D$F$_D$L$_D$-(2-Nal$_D$), f-M$_D$F$_D$I$_D$N$_D$R$_D$W$_D$L$_D$F$_D$S$_D$-(2-Nal$_D$), f-M$_D$F$_D$F$_D$ I$_D$N$_D$I$_D$LvT$_D$L$_D$-(2-Nal), f-A$_D$W$_D$K$_D$Y$_D$M$_D$V$_D$-(2-Nal$_D$), Ac-ML-(2-Nal)-(2-Nal$_D$), and Ac-M$_D$L$_D$-(2-Nal)-(2-Nal$_D$).

The C-terminal 2-NalD residue can be further modified by connection to a Tn antigen (N-acetylgalactosamine (GalNAc)) through a serine residue or at a side chain through a ε-amine of a lysine residue. Examples of these peptides include, without limitation, f-ML-(2-Nal)-(2-NalD)-(N-acetylgalactosamine, α1-O-(DL)-serine) and f-ML-(2-Nal)-(2-NalD)-Lys(ε-N-acetylgalactosamine, α1-O-(DL)-serine).

The peptides of the present invention can be synthesized using standard peptide synthesis operations. These include both FMOC (9-Fluorenylmethyloxy-carbonyl) and tBoc (tert-Butyl oxy carbonyl) synthesis protocols that can be carried out on automated solid phase peptide synthesis instruments including, without limitation, the Applied Biosystems 431A, 433A synthesizers and Peptide Technologies Symphony or large scale Sonata or CEM Liberty automated solid phase peptide synthesizers. This can be followed with standard HPLC purification to achieve a purified peptide product.

Also included in this invention are immunogenic conjugates that comprise an antigenic peptide conjugated to the peptides described herein. The antigenic peptide may include an epitope that induces an antibody or a T-cell mediated immune response.

The term "conjugate" is used herein to describe a chimeric moiety including at least two peptides covalently linked to one another directly or via a linker, via any bond type including a peptide bond. A conjugate can be prepared synthetically using solid phase techniques as a whole, or a conjugate can be prepared by covalently joining a first peptide to a second peptide post synthesis of the first and second peptides. For example, covalent linkages can be formed between amino acid side chains, including disulfide bond, sulfinyl linkage, and hydrocarbon or olefin bond. Formation of disulfide bonds, sulfinyl linkages, hydrocarbon and olefin bonds is well known in the art. Disulfide bonds are formed by a covalent coupling of thiol groups from a cysteine or cysteine derivative. Sulfinyl linkages can be formed by well-known procedures, either by oxidation of a disulfide bond with mCPBA (Chayajarus et al., "Efficient Synthesis of Carbohydrate Thionolactones," *Tetrahedron Lett.* 47:3517-3520 (2006), which is hereby incorporated by reference in its entirety) or by oxidation with dimethyl dioxirane (Bourles et al., "Direct Synthesis of a Thiolato-S and Sulfinato-S Co$^{III}$ Complex Related to the Active Site of Nitrile Hydratase: A Pathway to the Post-Translational Oxidation of the Protein," *Angew. Chem. Int. Ed.* 44:6162-6165 (2005), which is hereby incorporated by reference in its entirety). Olefin bonds can be formed by α-amino acids having an unsaturated hydrocarbon sidechain, such as allyl glycine, using known procedures including those disclosed in PCT Application Publ. No. WO 2004/101476, which is hereby incorporated by reference in its entirety.

Exemplary antigen that can be introduced into conjugates of the present invention include antigen of any pathogen, typically bacteria, viruses, fungi, protozoa, and parasites. The antigen is not exclusively an immunodominant antigen, but it certainly can be an immunodominant antigen.

In certain embodiments, more than one peptide can be provided. The peptides can be similar in structure, including overall length and amino acid sequence, but possess different conjugated agents as described above. For example, multiple antigen can be introduced into different conjugates, which can then be presented in a single formulation as described below. In alternative embodiments, the peptides can be structurally distinct, having different peptide lengths and different amino acid sequences, but those structures are nevertheless capable of self-assembly due to the structural compatibility of the aromatic amino acid residues in the different peptides.

A further aspect of the invention relates to a hydrogel composition that includes an aqueous medium and one or more peptides as described herein, wherein the peptides are capable of self-assembly to form nanofibrils. The hydrogel, once formed, can release the peptides into the aqueous medium over a period of time that exceeds about 12 or about 24 hours, preferably exceeding 36 hours or even 48 hours. The hydrogel composition may further include an additional agent selected from the group consisting of an antibiotic agent, a chemotherapeutic agent, an immunotherapeutic agent, and an antigenic agent that comprises an epitope that induces either an antibody mediated or T-cell mediated immune response. The additional agent, in this embodiment, is not necessarily a structural component of the nanofibril (unless it is present in the form of a conjugate as described above). Instead, the additional agent can be merely entrapped within the hydrogel structure in a manner which restrictions diffusion of such agents from the hydrogel during such time than the integrity of the hydrogel is maintained.

A hydrogel may be defined as a three-dimensional, hydrophilic or amphiphilic polymeric network capable of taking up a quantity of water, typically a large quantity of water. The networks are composed of homopolymers or copolymers, are insoluble due to the presence of covalent chemical or physical (ionic, hydrophobic interactions, entanglements) crosslinks. The crosslinks provide the network structure and physical integrity. Hydrogels exhibit a thermodynamic compatibility with water that allows them to swell in aqueous media. The chains of the network are connected in such a fashion that pores exist and that a substantial fraction of these pores are of dimensions between 1 nm and 1000 nm.

As used herein and is well-known in the art, the term "hydrogel" refers to a material that comprises fibrous networks formed of water-soluble natural or synthetic polymer chains, typically (though not exclusively) containing more than 95% water, often more than 96%, 97%, 98%, or 99% water.

A "fibrous network" refers to a set of connections formed between the plurality of fibrous components. Herein, the fibrous components are composed of peptide fibrils, each formed upon self-assembly of short peptide building blocks. The peptide can be present alone within the fibrous network, in the form of a conjugate as described above which is incorporated into the fibrous network, or a combination thereof.

A "supramolecular fiber" means a structure of thermodynamically stable micellar fiber formed by self-assembly of supramolecular monomers. In general, such supramolecular fibers are entangled to form gel in the generation process of a supramolecular hydrogel.

The term "supramolecular monomer" as used herein means a low molecular weight compound that can form supramolecular hydrogel and a supramolecular fiber, which is an expedient term used with an assumption that the supramolecular hydrogel corresponds to a polymer. It is not meant that polymerization is required in the process of formation of the supramolecular hydrogel. The supramolecular monomer may also be referred to as "supramolecular hydrogelator".

The term "gelling" or "gelation" means a thickening of the medium that may result in a gelatinous consistency and even in a solid, rigid consistency that does not flow under its own weight.

A "gelator" is defined herein to include a non-polymeric organic compound whose molecules can establish, between themselves, at least one physical interaction leading to a self-assembly of the molecules in a carrier fluid to form a gel. The gel may result from the formation of a network of molecular nanofibers due to the stacking or aggregation of gelator molecules.

A "molecular nanofiber" is defined as a fiber with a diameter on the order of about 100 nanometers or less. The fibrous network can include nanofibers as well as fibers that have larger diameters. In certain embodiments, the hydrogel can contain a large majority of self-assembled, nanofibers, from about 60% or more, about 70% or more, about 80% or more, and even about 90% or more.

The principle and mechanism of peptide self-assembly has led to the development of supramolecular nanofibrils and hydrogels (Estroff et al., *Chem. Rev.,* 104, 1201-1218 (2004); Aida et al., *Science,* 335, 813-817 (2012); Branco et al., *Curr. Opin. Chem. Biol.,* 15, 427-434 (2011), each of which is hereby incorporated by reference in its entirety) of bioactive molecules as "self-delivery drugs" (Zhao et al., Chem. Soc. Rev., 38, 883-891 (2009), which is hereby incorporated by reference in its entirety). The development of supramolecular hydrogels affords a unique depot for controlled release (Zhao et al., *Chem. Soc. Rev.,* 38, 883-891 (2009); Cherif-Cheikh et al., *Proc. Int. Symp. Control. Rel. Bioact. Mater.,* 25, 798-799 (1998); Maji et al., *PLoS Biol.,* 6, ell (2008); Vemula et al., *Biomaterials,* 30, 383-393 (2009), each of which is hereby incorporated by reference in its entirety). Intrigued by the simplicity and effectiveness of the "self-delivery drugs," also from the perspectives of peptide engineering and peptide formulation, it is believed based on the data presented herein that, by rational chemical derivatization, fMLF-derived peptides can form supramolecular hydrogels without compromising the biological efficacy of fMLF, and the corresponding hydrogels can deliver long-term efficacy for local accumulation of neutrophils by sustained release of the chemotactic hydrogelators. FIG. 1 illustrates one approach for converting the peptide fMLF to an fMLF-based hydrogelator 3, which as demonstrated in the Examples is capable of inducing chemotaxis of neutrophils in vitro and accumulation of neutrophils in vivo.

In certain embodiments, the carrier used to form the hydrogel is an aqueous medium that is well tolerated for administration to an individual, typically a sterile isotonic aqueous buffer. Exemplary aqueous media include, without limitation, normal saline (about 0.9% NaCl), phosphate buffered saline (PBS), sterile water/distilled autoclaved water (DAW), as well as cell growth medium (e.g., MEM, with or without serum), aqueous solutions of dimethyl sulfoxide (DMSO), polyethylene glycol (PEG), and/or dextran (less than 6% per by weight).

To improve patient tolerance to administration, the pharmaceutical composition preferably has a pH of about 6 to about 8, preferably about 6.5 to about 7.4. Typically, sodium hydroxide and hydrochloric acid are added as necessary to adjust the pH.

The pharmaceutical composition suitably includes a weak acid or salt as a buffering agent to maintain pH. Citric acid has the ability to chelate divalent cations and can thus also prevent oxidation, thereby serving two functions as both a buffering agent and an antioxidant stabilizing agent. Citric acid is typically used in the form of a sodium salt, typically 10-500 mM. Other weak acids or their salts can also be used.

The pharmaceutical composition may also include solubilizing agents, preservatives, stabilizers, emulsifiers, and the like. A local anesthetic (e.g., lidocaine) may also be included in the compositions, particularly for injectable forms, to ease pain at the site of the injection.

Effective amounts of the peptide will depend on the nature of use, including the nature of the cancerous condition which is being treated, tumor volume and stage, and its location(s). By way of example only, suitable peptide concentrations may range from about 1 µM to about 10 mM, preferably about 10 µM to about 5 mM, about 50 µM to about 2 mM, or about 100 µM to about 1 mM. The volume of the pharmaceutical composition administered, and thus, dosage of the peptide administered can be adjusted by one of skill in the art to achieve optimized results. By way of example, 800 µg per day, repeated every third day, may be effective. This can be adjusted lower to identify the minimal effective dose, or tailored higher or lower according to the nature of the tumor to be treated.

To make the hydrogel compositions of the present invention, a method is provided wherein the peptides as described hereinabove can be introduced into an aqueous medium of the types described above for the carrier, whereby the peptides self-assemble to form nanofibrils. The peptides can further be introduced into the aqueous solution at a concentration of less than about 10 percent w/v, less than about 5 percent w/v or less than about 3 percent w/v. The method further includes introducing into the aqueous medium an agent selected from the group consisting of an antibiotic agent, a chemotherapeutic agent, an immunotherapeutic agent, and an antigenic agent that comprises an epitope that induces either an antibody mediated or T-cell mediated immune response. The introducing of an agent can be carried out prior or after introducing the peptides. Alternatively, the introducing of the agent and peptides can be carried out simultaneously.

The hydrogel compositions of the present invention are particularly useful in a number of important therapeutic areas.

In one embodiment, the hydrogel compositions of the present invention can be used in a method for eliciting a prolonged inflammatory response in a subject. This method includes administering to a subject in need thereof a therapeutically effective amount of the hydrogel compositions as described herein. Using this method, the administration of the hydrogel composition can be carried out parenterally, subcutaneously, intravenously, intramuscularly, intraperitoneally, by implantation, by intracavitary or intravesical instillation, intraarterial, intralesionally, intradermally, peritumorally, intratumorally, or by introduction into one or more lymph nodes. Upon administration, release of the peptides over time from the hydrogel affords a formyl peptide chemotractant that induces neutrophil accumulation at the site of administration and, thus, a prolonged inflammatory response that is maintained over the course of peptide release from the hydrogel.

In another embodiment, the hydrogel compositions of the present invention can be used in a method for eliciting prolonged neutrophil accumulation in vivo. This method includes administering to a subject in need thereof a therapeutically effective amount of the hydrogel compositions as described herein, wherein the administering is effective to release the formyl peptide over a period of time exceeding about 12 or about 24 hours, preferably exceeding 36 hours or even 48 hours, thereby inducing prolonged neutrophil accumulation at the site of administration. Administration of the hydrogel compositions can be accomplished using the modes of delivery identified above.

In a further embodiment, the hydrogel compositions of the present invention can be used in a method for treating a cancerous condition. This method includes administering to a subject having a cancerous condition a therapeutically effective amount of the hydrogel compositions as described herein, wherein the administering is effective to inhibit tumor growth or shrink tumor size. The administration of the hydrogel compositions may be carried out intralesionally, intratumorally, intradermally, or peritumorally. The administration can also be repeated over a period of time so as to help maintain the neutrophil accumulation at the site of the tumor and thereby promote an innate immune response against the tumor.

Use of the hydrogel compositions in combination with other cancer therapeutic agents is also contemplated. These other cancer therapeutics include, without limitation, chemotherapeutic agents, radiotherapy, immunotherapy, and surgical therapy. Optimization of hydrogel composition administration in combination with these other therapies can be achieved with routine skill.

Another aspect of the present invention relates to a formyl peptide receptor antagonist peptide that is capable of self-assembly to form a hydrogel. A peptide according to this aspect of the invention includes include up to about 35 amino acids and has a tert-butyloxycarbonylated (t-Boc) or ureido N-terminal residue and a C-terminal residue selected from the group of 2-Nal or 2-Nal$_D$. The amino acids can all be D-amino acids or a mixture of L-amino acids and D-amino acids.

In one embodiment, the C-terminal residue of the peptide is 2-Nal$_D$.

The peptide length, as used herein, is up to about 35 amino acids, up to about 30 amino acids, up to about 25 amino acids, up to about 20 amino acids, up to about 15 amino acids, up to about 10 amino acids or between 3 to 10 amino acids. The peptides can include all D-amino acids, all L-amino acids, or a mixture of L-amino acids and D-amino acids. In preferred embodiments, the peptide includes only D-amino acids or a mixture of D-amino acids and L-amino acids where the D-amino acid content is greater than 50%, 60%, 70%, 80%, 90%, or 95%.

The amino acids residues intermediate the N-terminal and C-terminal residues identified above can be any amino acid, including naturally and non-naturally occurring amino acids. In accordance with one embodiment, amino acids near the C-terminal residue are aromatic. The aromatic side chains cooperate with the C-terminal residue to facilitate self-assembly into fibrils and, hence, gelation. The aromatic amino acids used in the peptides of the present invention include, without limitation, any one or more of phenylalanine, phenylalanine derivatives, tyrosine, tyrosine derivatives, tryptophan, and tryptophan derivatives. Any known or hereinafter developed phenylalanine derivatives, tyrosine derivatives, or tryptophan derivatives can be used in the present invention. Derivatives of these amino acids include the addition of one or more ring substituents.

As a consequence of utilizing entirely D-amino acids or a high proportion of D-amino acids, it is possible to render the peptide protease resistant, e.g., resistant to proteinase K digestion. Presence of the C-terminal 2-Nal$_D$ residue promotes enhanced resistance to proteinase digestion.

The inventive peptides are capable of self-assembling to form hydrogels upon introduction into an aqueous solution and are present in concentrations up to about 10 w/v %, up to about 5 w/v % or between 0.1 and 3 w/v %.

Examples of these peptides include, without limitation, tBoc-Phe-Leu-(2-Nal$_D$)-Leu-(2-Nal$_D$) and various N-ureido peptides including benzyl-NH(CO)-ML-(2-Nal)-(2-Nal$_D$), phenyl-NH(CO)-ML-(2-Nal)-(2-Nal$_D$), 2-allyl-NH(CO)-ML-(2-Nal)-(2-Nal$_D$), m-tolyl-NH(CO)-ML-(2-Nal)-(2-Nal$_D$), p-tolyl-NH(CO)-ML-(2-Nal)-(2-Nal$_D$), 4-chlorophenyl-NH(CO)-ML-(2-Nal)-(2-Nal$_D$), 4-methoxyphenyl-NH(CO)-ML-(2-Nal)-(2-Nal$_D$), isopropyl-NH(CO)-ML-(2-Nal)-(2-Nal$_D$), n-propyl-NH(CO)-ML-(2-Nal)-(2-Nal$_D$), tert-butyl-NH(CO)-ML-(2-Nal)-(2-Nal$_D$), and n-butyl-NH(CO)-ML-(2-Nal)-(2-Nal$_D$).

These peptides can be synthesized using the same peptide synthesis processes and purification procedures described above.

Hydrogel compositions may also be formed using an aqueous medium and peptides having a t-Boc or ureido N-terminal residue and a C-terminal 2-Nal or 2-Nal$_D$ residue, wherein the peptides can self-assemble to form nanofibrils. In one embodiment, the hydrogel can release the peptides into the aqueous medium over a period of time that exceeds about 12 hours or about 24 hours.

In yet another embodiment, there is also a method for making the hydrogel composition comprising introducing a peptide into an aqueous medium, wherein the peptide has a t-Boc or ureido N-terminal residue and a C-terminal 2-Nal or 2-Nal$_D$ residue and is capable of self-assembly to form nanofibrils. The aqueous medium can be in form of water or a buffered solution. In addition, the peptide can be introduced into the aqueous solution at a concentration of less than about 10 percent w/v, less than about 5 percent w/v or less than about 3 percent w/v. The method for making the hydrogel may further include introducing into the aqueous medium an agent selected from the group consisting of an antibiotic agent, a chemotherapeutic agent, and an immunotherapeutic agent. The introducing of the agent can be carried out prior to introducing the peptide or after introducing the peptide. Alternatively, both agent and peptide can be introduced simultaneously.

These peptides, hydrogels, and pharmaceutical compositions of the present invention find a number of uses, including their administration in an effective amount at an inflammation site in a subject so as to decrease neutrophil accumulation, decrease neutrophil toxicity, and otherwise inhibit neutrophil chemotactic migration. In many autoimmune diseases, neutrophils can be found at primary sites of inflammation. For example, in the rheumatoid joint, neutrophils can be found both in synovial tissue and in joint fluid, where they have a huge potential to directly inflict damage to tissue, bone and cartilage via the secretion of proteases and toxic oxygen metabolites, as well as drive inflammation through antigen presentation and secretion of cytokines, chemokines, prostaglandins and leucotrienes. See Wright et al., "Neutrophil Function in Inflammation and Inflammatory Diseases," *Rheumatology* 49:1618-1631 (2010), which is hereby incorporated by reference in its entirety. As explained in PCT Publ. No. WO 2010/141584, which is hereby incorporated by reference in its entirety, formyl peptide receptor antagonists can be used to treat a number of conditions characterized by undesirable neutrophil activation, including cystic fibrosis, inflammatory bowel disease, and Crohn's Disease. In addition, these peptides, hydrogels, and pharmaceutical compositions can be used to decrease the pain caused by formyl peptides secreted by some bacteria.

In these methods of the present invention, a subject is administered a therapeutically effective amount of the hydrogel composition (containing the peptides having a t-Boc N-terminal residue and a C-terminal 2-Nal or 2-Nal$_D$ residue, and capable of self-assembles to form nanofibrils), wherein said administering is effective to release the peptide over a period of time exceeding about 12 hours, thereby inhibiting prolonged neutrophil accumulation at the site of administration, inhibiting neutrophil toxicity at the site of administration, and inhibiting chemotactic migration of neutrophils at the site of administration. Administration can be achieved using any of the modes of delivery described above, but preferably the route for administration involves directly targeting a site of inflammation. In CF, this includes the airways of the lungs, and in IBD and Crohn's Disease this includes the intestinal tract.

Yet another aspect of the present invention relates to a third structurally distinct peptide (or peptidomimetic that includes a peptide component). In this aspect, the peptide component includes up to about 35 amino acids. Attached at the N-terminal end of the peptide component is a deformylase inhibitor component; the peptide component also comprises a C-terminal residue selected from the group of 2-Nal or 2-Nal$_D$. The amino acids in the peptide component can all be D-amino acids or a mixture of L-amino acids and D-amino acids.

In one embodiment, the C-terminal residue of the peptide is 2-Nal$_D$.

The peptide length, as used herein, is up to about 35 amino acids, up to about 30 amino acids, up to about 25 amino acids, up to about 20 amino acids, up to about 15 amino acids, up to about 10 amino acids or between 3 to 10 amino acids. In certain embodiments, the peptide component can even be a single amino acid. The peptides can include all D-amino acids, all L-amino acids, or a mixture of L-amino acids and D-amino acids. In preferred embodiments, the peptide includes only D-amino acids or a mixture of D-amino acids and L-amino acids where the D-amino acid content is greater than 50%, 60%, 70%, 80%, 90%, or 95%.

The amino acids residues intermediate the N-terminal and C-terminal residues identified above can be any amino acid, including naturally and non-naturally occurring amino acids. In accordance with one embodiment, amino acids near the C-terminal residue are aromatic. The aromatic side chains cooperate with the C-terminal residue to facilitate self-assembly into fibrils and, hence, gelation. The aromatic amino acids used in the peptides of the present invention include, without limitation, any one or more of phenylalanine, phenylalanine derivatives, tyrosine, tyrosine derivatives, tryptophan, and tryptophan derivatives. Any known or hereinafter developed phenylalanine derivatives, tyrosine derivatives, or tryptophan derivatives can be used in the present invention. Derivatives of these amino acids include the addition of one or more ring substituents.

As a consequence of utilizing entirely D-amino acids or a high proportion of D-amino acids, it is possible to render the peptide or peptidomimetic protease resistant, e.g., resistant to proteinase K digestion. Presence of the C-terminal 2-Nal$_D$ residue promotes enhanced resistance to proteinase digestion.

The inventive peptides or peptidomimetics are capable of self-assembling to form hydrogels upon introduction into an aqueous solution and are present in concentrations up to about 10 w/v %, up to about 5 w/v % or between 0.1 and 3 w/v %.

In one embodiment, the N-terminal deformylase inhibitor component is a derivative of GSK1322322 (N-[(2R)-3-[2-[6-[(9aS)-3,4,6,7,9,9a-hexahydro-1H-pyrazino[2,1-c][1,4]oxazin-8-yl]-5-fluoro-2-methylpyrimidin-4-yl] hydrazinyl]-2-(cyclopentylmethyl)-3-oxopropyl]-N-hydroxyformamide) having a structure:

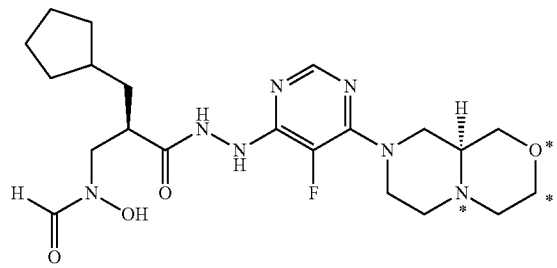 [SMILES: O=CN(O)C[C@@H](CC1CCCC1)C(=O)NNc1ncnc(N2CCN3CCOC[C@@H]3C2)c1F]

where the asterisks identify sites for derivatization to couple the N-terminal residue of the peptide component or the 2-Nal or 2-Nal$_D$ residue. FIG. 9A illustrates one example for coupling 2-Nal$_D$ to the pyrazino[2,1-c][1,4]oxazine ring at the 1-N position, where the synthesis steps can be carried out in the manner described by Heuisul, P. et al. (*Bioorg. Med. Chem. Lett.*, 18, 2900-2904 (2008) and Kaldor et al., *J. Org. Chem.*, 66, 3495-3501 (2001), respectively, which are hereby incorporated by reference in their entirety. Alternative derivatives of GSK1322322 at the 3-C position and 4-O position are also shown in FIG. 9B.

In another embodiment, the N-terminal deformylase inhibitor may have a structure according to Formula I:

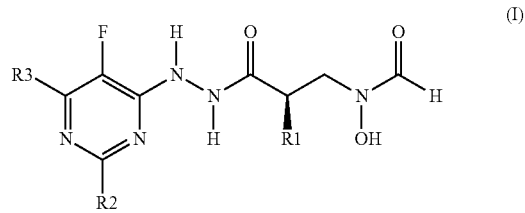

wherein
R1 is selected from the group consisting of C2-C7 alkyl and —(CH2)n-C3-C6 cycloalkyl;
R2 is selected from the group consisting of C1-C3 alkyl; cyclopropyl; C1-C3 alkoxy; C1-C3 haloalkyl; C1-C3 sulfanyl; 5-membered heteroaryl; 5-membered heterocycloalkyl; halo; hydroxymethyl; and —NRaRb;
R3 is a phenyl or heteroaryl linking group, each optionally substituted by one to three R6 groups and including a peptide bond that links the structure of Formula (I) to the C-terminal residue;
R4 is selected from the group consisting of H; C1-C6 alkyl, optionally substituted with one or two R7 groups; C1-C6 alkoxy; C3-C6 cycloalkyl, optionally substituted with one to three R6 groups; heterocycloalkyl, optionally substituted by one to three R6 groups; heteroaryl, optionally substituted by one to three R6 groups; and phenyl, optionally substituted by one to three R6 groups;
R5 is selected from H; C1-C6 alkyl, optionally substituted with one or two R7 groups; C1-C6 alkoxy; C3-C6 cycloalkyl, optionally substituted with one to three R6 groups; heterocycloalkyl, optionally substituted by one to three R6 groups; heteroaryl, optionally substituted by one to three R6 groups; and phenyl, optionally substituted by one to three R6 groups;

or R4 and R5 are joined together with the N-atom to which they are attached, forming a heterocycloalkyl group optionally substituted with one to three R6 groups;

each R6 is independently selected from the group consisting of C1-C6 alkyl, optionally substituted with one to three R7 groups; hydroxy; C1-C3 alkoxy; —C(O)NRaRb; —C(O)Rc; —C(O)ORc; heterocycloalkyl; C3-C6 cycloalkyl optionally substituted with one —NRaRb or pyrrolidinyl; oxo; cyano; —NRaRb; phenyl; heteroaryl; and halo;

each R7 is independently selected from the group consisting of hydroxy; C1-C3 alkoxy; halo; phenyl; cyano; —NRaRb; —C(O)NRaRb; —C(O)Rc; C3-C6 cycloalkyl, optionally substituted with one hydroxy, heterocycloalkyl or —NRaRb group; heterocycloalkyl; and heteroaryl optionally substituted with one methyl, —NRaRb or hydroxy;

each Ra is independently selected from the group consisting of H and C1-C3 alkyl optionally substituted with one hydroxy, methoxy, or dimethylamine;

each Rb is independently selected from the group consisting of H and C1-C3 alkyl;

each Rc is independently selected from the group consisting of C1-C3 alkyl optionally substituted with one methoxy group; phenyl; heterocycloalkyl; heteroaryl; and an amino acid sequence that links the structure of Formula (I) to the C-terminal residue, and n is an integer from 0 to 2.

Examples of these peptides or peptidomimetics having an N-terminal deformylase inhibitor component and a C-terminal residue such as 2-Nal or 2-Nal$_D$ are GSK1322322-(2-Nal$_D$) Peptide 1, GSK1322322-(2-Nal$_D$) Peptide 2 and GSK1322322-(2-Nal$_D$) Peptide 3 illustrated in FIG. 9B.

Hydrogel compositions may also be formed using an aqueous medium and peptides or peptidomimetics having an N-terminal deformylase inhibitor component as described above, wherein the peptides or peptidomimetics can self-assemble to form nanofibrils. In one embodiment, the hydrogel can release the peptides or peptidomimetics into the aqueous medium over a period of time that exceeds about 12 hours, about 24 hours, about 36 hours, or more.

In yet another embodiment, there is also a method for making the hydrogel composition according to this aspect of the invention by introducing a peptide or peptidomimetic into an aqueous medium, wherein the peptide or peptidomimetic includes the N-terminal deformylase inhibitor component as described above, and the peptide or peptidomimetic is capable of self-assembling to form nanofibrils. The method for making the hydrogel may further include introducing into the aqueous medium an agent selected from the group consisting of an antibiotic agent, a chemotherapeutic agent, an immunotherapeutic agent, and an antigenic agent that comprises an epitope that induces either an antibody mediated or T-cell mediated immune response. The introducing of the agent can be carried out prior to introducing the peptide or peptidomimetic, or after introducing the peptide or peptidomimetic. Alternatively, both the agent and the peptide or peptidomimetic can be introduced simultaneously.

In yet another embodiment, there is also a method of treating a bacterial infection comprising administering to a subject having a bacterial infection a therapeutically effective amount of the hydrogel composition as described hereinabove, wherein the administering is effective to treat the bacterial infection. Administration can be carried out using the modes for administration described elsewhere herein, but in certain embodiments the administration of the hydrogel is carried out directly to the site of infection. In this case, administration can be used to treat sepsis, which includes reducing the severity of sepsis conditions and promoting resolution of the septic condition. See Kim et al., "The Agonists of Formyl Peptide Receptors Prevent Development of Severe Sepsis after Microbial Infection," *J. Immunol.* 185:4302-4310 (2010), which is hereby incorporated by reference in its entirety.

In certain embodiments, the hydrogel includes a peptide comprising up to about 35 amino acids, wherein the amino acids include a formylated or acetylated N-terminal residue and a C-terminal residue selected from the group of 2-Nal or 2-Nal$_D$.

In alternative embodiments, the hydrogel includes a peptide or peptidomimetic having an N-terminal deformylase inhibitor component as described above.

The bacterial infection may involve biofilm formation, wherein the biofilm is formed on a prosthetic device. The bacterial infection can be an ear infection, a sinusitis, an upper and lower respiratory tract infection, a genital infection, a skin infection, a soft tissue infection, a bacterial endocarditis or an infection resulting from a medical or dental procedure.

The bacteria can be a Gram positive or a Gram negative aerobic or anaerobic bacterium selected from the genera consisting of *Streptococcus, Staphylococcus, Moraxella, Haemophilus, Neisseria, Mycoplasma, Legionella, Chlamydia, Bacteroides, Clostridium, Fusobacterium, Propionibacterium*, and *Peptostreptococcus*.

Additional Definitions

"Treating" is used herein to refer to any treatment of, or prevention of, or inhibition of a disorder or disease or infection in a subject and includes by way of example: (a) preventing the disease or disorder from occurring in a subject that may be predisposed to the disease or disorder, but has not yet been diagnosed as having it; (b) inhibiting the disease or disorder or infection, i.e., arresting its progression; or (c) relieving or ameliorating the disease or disorder or infection, i.e., slowing progression of the disease, disorder, or infection, or causing regression or complete resolution.

As used herein, "chemoattractant" refers to a substance that elicits directional migration of cells in response to the concentration gradient of the molecule. Chemoattractants are important immunomodulators. One example of cells that respond to a chemoattractant is a neutrophil.

An antigenic agent may be any of the great variety of agents that are administered to a subject to elicit an immune response in the subject. An antigenic agent may be an immunogen derived from a pathogen. The antigenic agent may be, for example, a peptide or protein antigen, a viral antigen or polypeptide, an inactivated virus, a recombinant virus, a bacterial or parasitic antigen, an inactivated bacteria or parasite, a whole cell, a genetically modified cell, a tumor associated antigen or tumor cell, a toxin, a lipid, a glycolipid, a glycoprotein, or a carbohydrate antigen. In some applications an antigen is not a living cell. In some embodiments, an antigenic agent is a soluble antigen. Antigenic agents can be immunogenic agents available as vaccine components. Such vaccines may include, but are not limited to, antigenic vaccines components directed against various infectious, viral, and parasitic diseases, toxins, and anti-tumor vaccine components. Antitumor vaccines include, but are not limited to, peptide vaccines, whole cell vaccines, genetically modified whole cell vaccines, lipid vaccines, glycolipid vaccines, glycoprotein vaccines, recombinant protein vaccines or vaccines based on expression of tumor associated antigens by recombinant viral vectors.

As used herein, the term "subject" includes, but is not limited to, humans and non-human vertebrates. In some embodiments, a subject is a mammal, particularly a human. A subject may be an "individual," "patient," or "host." A subject may include, for example, a human, a higher primate, a non-human primate, domestic livestock and domestic pets (such as dogs, cats, cattle, horses, pigs, sheep, goats, mules, donkeys, mink, and poultry), laboratory animals (such as for example, mice, rats, hamsters, guinea pigs, and rabbits), and wild life.

In certain embodiments, the present invention relates to any one of the aforementioned compounds or supramolecular hydrogels for use in the manufacture of a medicament for treating cancer, tumors, malignancies, neoplasms, or other dysproliferative diseases.

Examples of cancers, tumors, malignancies, neoplasms, and other dysproliferative diseases that can be treated according to the invention include leukemias, such as myeloid and lymphocytic leukemias, lymphomas, myeloproliferative diseases, and solid tumors, such as but not limited to sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

In certain embodiments, the present invention relates to any one of the aforementioned compounds or supramolecular hydrogels for use in the treatment of bacterial infections. The bacterial infection may involve formation of a biofilm, e.g., on a prosthetic device or other organ or tissue surface. The bacterial infection may include one or more of ear infections, sinusitis, upper and lower respiratory tract infections, genital infections, skin and soft tissue infections, bacterial endocarditis, medical device-related infections or infections resulting from medical or dental procedures. The bacterial infection may involve Gram positive or Gram negative aerobic or anaerobic bacteria from various genera including, without limitation, *Streptococcus*, e.g. *S. pneumoniae* and *S. pyogenes*, *Staphylococcus*, e.g. *S. aureus*, *S. epidermidis*, and *S. saprophyticus*, *Moraxella*, e.g. *M. catarrhalis*, *Haemophilus*, e.g. *H. influenzae*, *Neisseria*, *Mycoplasma*, e.g. *M. pneumoniae*, *Legionella*, e.g. *L. pneumophila*, *Chlamydia*, e.g. *C. pneumoniae*, *Bacteroides*, *Clostridium*, *Fusobacterium*, *Propionibacterium*, and *Peptostreptococcus*.

Pharmaceutical Compositions

One or more compounds of the present invention (i.e., peptides or peptidomimetic, or a plurality thereof) can be administered to a human patient alone or in pharmaceutical compositions where they are mixed with biologically suitable carriers or excipient(s) at doses to treat or ameliorate a disease or condition as described herein. Mixtures of these compounds can also be administered to the patient as a simple mixture or in suitable formulated pharmaceutical compositions. For example, one aspect of the invention relates to pharmaceutical composition comprising a therapeutically effective dose of a peptide (or peptidomimetic), a nanofiber or gel prepared therefrom, or a pharmaceutical composition containing the same in a pharmaceutically acceptable diluent or carrier.

Suitable routes of administration may, for example, include oral, eyedrop, rectal, transmucosal, topical, or intestinal administration; parenteral delivery, including intramuscular, subcutaneous, intramedullary injections, as well as intrathecal, direct intraventricular, intravenous, intraperitoneal, intranasal, or intraocular injections. Administration can also be carried out by implantation, by intracavitary or intravesical instillation, intraarterially, intralesionally, intradermally, peritumorally, intratumorally, or by introduction into one or more lymph nodes.

Alternatively, one may administer the compounds of the present invention (i.e., peptides or peptidomimetic, or a plurality thereof) in a local rather than a systemic manner, for example, via injection of the compound directly into an edematous site.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. Proper formulation is dependent upon the route of administration chosen.

For injection, the compounds (i.e., peptides or a plurality of peptides) of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds (i.e., peptides or a plurality of peptides) can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions containing the compounds (i.e., peptides or a plurality of peptides) may take the form of tablets or lozenges formulated in conventional manner.

For administration by inhalation, the compounds (i.e., peptides or a plurality of peptides) for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds of the present invention (i.e., peptides or peptidomimetic, or a plurality thereof) can be formulated for parenteral administration by injection, e.g., bolus injection or continuous infusion. Formulations for injection may be presented in unit dosage form, e.g., in ampoules or in multi-dose containers, with an added preservative. The compositions may take such forms as suspensions, solutions or emulsions in aqueous vehicles, and may contain formulatory agents such as suspending, stabilizing and/or dispersing agents.

Pharmaceutical formulations for parenteral administration include aqueous solutions of the active compounds (i.e., peptides or a plurality of peptides) in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds of the present invention (i.e., peptides or peptidomimetic, or a plurality thereof) may also be formulated in rectal compositions such as suppositories or retention enemas, e.g., containing conventional suppository bases such as cocoa butter or other glycerides.

In addition to the formulations described previously, the compounds of the present invention (i.e., peptides or peptidomimetic, or a plurality thereof) may also be formulated as a depot preparation. Such long acting formulations may be administered by implantation (for example subcutaneously or intramuscularly or by intramuscular injection). Thus, for example, the compounds may be formulated with suitable polymeric or hydrophobic materials in addition to the hydrogel component (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds of the present invention (i.e., peptides or peptidomimetic, or a plurality thereof) may be provided as salts with pharmaceutically compatible counterions (i.e., pharmaceutically acceptable salts). A "pharmaceutically acceptable salt" means any non-toxic salt that, upon administration to a recipient, is capable of providing, either directly or indirectly, a compound or a prodrug of a compound of this invention. A "pharmaceutically acceptable counterion" is an ionic portion of a salt that is not toxic when released from the salt upon administration to a recipient. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

Acids commonly employed to form pharmaceutically acceptable salts include inorganic acids such as hydrogen bisulfide, hydrochloric, hydrobromic, hydroiodic, sulfuric and phosphoric acid, as well as organic acids such as para-toluenesulfonic, salicylic, tartaric, bitartaric, ascorbic, maleic, besylic, fumaric, gluconic, glucuronic, formic, glutamic, methanesulfonic, ethanesulfonic, benzenesulfonic, lactic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, .beta.-hydroxybutyrate, glycolate, maleate, tartrate, methanesulfonate, propanesulfonate, naphthalene-1-sulfonate, naphthalene-2-sulfonate, mandelate and the like salts. Preferred pharmaceutically acceptable acid addition salts include those formed with mineral acids such as hydrochloric acid and hydrobromic acid, and especially those formed with organic acids such as maleic acid.

Suitable bases for forming pharmaceutically acceptable salts with acidic functional groups include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine;

N-methyl, N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N-di alkyl-N-(hydroxy alkyl)-amines, such as N,N-dimethyl-N-(2-hydroxyethyl)amine, or tri-(2-hydroxyethyl)amine; N-methyl-D-glucamine; and amino acids such as arginine, lysine, and the like.

Combination Therapy

In one embodiment of the invention, a hydrogel composition, or a pharmaceutically acceptable salt thereof, can be used alone or in combination with another therapeutic agent to treat diseases such as cancer. It should be understood that the compounds (i.e., peptide or a plurality of peptides) of the invention can be used alone or in combination with an additional agent, e.g., a therapeutic agent, said additional agent being selected by the skilled artisan for its intended purpose. For example, the additional agent can be a therapeutic agent that is art-recognized as being useful to treat the disease or condition being treated by the compound (i.e., peptide or a plurality of peptides) of the present invention. The additional agent also can be an agent that imparts a beneficial attribute to the therapeutic composition e.g., an agent that affects the viscosity of the composition. The additional agent may be selected from the group consisting of an antibiotic agent, a chemotherapeutic agent, an immunotherapeutic agent, and an antigenic agent that comprises an epitope that induces either an antibody mediated or T-cell mediated immune response.

The combination therapy contemplated by the invention includes, for example, administration of the peptide or a plurality of peptides of the invention, or a pharmaceutically acceptable salt thereof, and additional agent(s) in a single pharmaceutical formulation as well as administration of a compound (i.e., peptide or a plurality of peptides) of the invention, or a pharmaceutically acceptable salt thereof, and additional agent(s) in separate pharmaceutical formulations. In other words, co-administration shall mean the administration of at least two agents to a subject so as to provide the beneficial effects of the combination of both agents. For example, the agents may be administered simultaneously or sequentially over a period of time.

It should further be understood that the combinations included within the invention are those combinations useful for their intended purpose. The combination can also include more than one additional agent, e.g., two or three additional agents if the combination is such that the formed composition can perform its intended function.

As used herein, a "therapeutically effective amount" or "therapeutically effective dose" is an amount of a compound or compounds (i.e., peptides or a plurality of peptides) of the invention or a combination of two or more such compounds, which sufficiently result to the inhibition, totally or partially, the progression of the condition or alleviation, at least partially, of one or more symptoms of the condition. A therapeutically effective amount can also be an amount which is prophylactically effective. The amount which is therapeutically effective will depend upon the patient's size and gender, the condition to be treated, the severity of the condition and the result sought. For a given patient, a therapeutically effective amount can be determined by methods known to those of skill in the art.

Toxicity and therapeutic efficacy of such compounds can be determined by standard pharmaceutical procedures in cell cultures or experimental animals, e.g., for determining the maximum tolerated dose (MTD) and the $ED_{50}$ (effective dose for 50% maximal response). The dose ratio between toxic and therapeutic effects is the therapeutic index and it can be expressed as the ratio between MTD and $ED_{50}$. The data obtained from these cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. The exact formulation, route of administration and dosage can be chosen by the individual physician in view of the patient's condition. (See e.g., Fingl et al., 1975, in "The Pharmacological Basis of Therapeutics", Ch. 1, p. 1, which is hereby incorporated by reference in its entirety). In the treatment of crises, the administration of an acute bolus or an infusion approaching the MTD may be required to obtain a rapid response.

The methods of the present invention may include in vitro, ex vivo, or in vivo methods. The preparation of the hydrogel is effected prior to its application to a desired application site. Thus, for example, when the desired application site is a bodily organ or cavity, the hydrogel is prepared ex vivo, prior to its application, by contacting the peptide or plurality of peptides and an aqueous solution, as described hereinabove, and is administered subsequent to its formation.

Alternatively, the preparation of the hydrogel can also be performed upon its application, such that the peptides or plurality of peptides and the aqueous solution are each applied separately to the desired site and the hydrogel is formed upon contacting the peptides and the aqueous solution at the desired site of application. Thus, for example, contacting the peptides or plurality of peptides and the aqueous solution can be performed in vivo, such that the peptides or plurality of peptides and the aqueous solution are separately administered.

According to these embodiments, the administration is preferably effected locally, into a defined bodily cavity or organ, where peptides or plurality of peptides and the aqueous solution become in contact while maintaining the desired ratio there between that would allow the formation of a hydrogel within the organ or cavity. As discussed hereinabove, the peptides or plurality of peptides can be utilized either per se, or, optionally and preferably, be dissolved in a water or any aqueous solvent.

Kits

According to another aspect of the present invention, there is provided a kit for forming the hydrogel described herein which comprises a peptide or a plurality of peptides, as described herein and an aqueous solution, as described herein, each being individually packaged within the kit, wherein the peptide or plurality of peptides and the solution are selected such that upon contacting the plurality of peptides and the solution, a hydrogel comprising a fibrous network of the peptide or plurality of peptides, as described herein, is formed.

Such a kit can be utilized to prepare the hydrogel described herein at any of the desired site of actions (e.g., a bodily cavity or organ) described hereinabove.

The kit can be designed such that the peptides or peptidomimetic (or a plurality thereof) and the aqueous solution would be in such a ratio that would allow the formation of the hydrogel at the desired site of application.

As used herein, the phrases "desired site of application" and "desired application site" describe a site in which application of the hydrogel described herein is beneficial, namely, in which the hydrogel can be beneficially utilized for therapeutic uses, as described in detail hereinbelow.

Such a kit can further comprise an additional active agent, as is detailed herein, which is to be attached to or encapsulated in the hydrogel, upon its formation, so as to form the composition-of-matter described herein.

The additional active agent can be individually packaged within the kit or can be packaged along with the peptide or plurality of peptides or along with the aqueous solution.

As is further demonstrated in the Examples section that follows, the hydrogels formed according to the present invention are characterized by exceptional material properties, which render them highly advantageous for use in applicative technologies.

EXAMPLES

The following examples are provided to illustrate embodiments of the present invention but are by no means intended to limit its scope.

Materials and Methods for Example 1-5

Synthesis: Chemical reagents and solvents were used as received from commercial sources. The peptide synthesis was described previously in details (Gao et al., Nat. Commun., 3, 1033 (2012), which is hereby incorporated by reference in its entirety). Briefly, the peptides were synthesized by standard Fmoc solid-phase peptide synthesis and formylated by 2,2,2-trifluoroethyl formate (Hill et al., Org. Lett., 4, 111-113 (2001), which is hereby incorporated by reference in its entirety). The peptides were purified by a Waters Delta600 HPLC system equipped with an in-line diode array UV detector using a XTerra C18 RP column with CH3CN (0.1% of trifluoroacetic acid) and water (0.1% of trifluoroacetic acid) as the eluent. 1H NMR and 13C NMR spectra were obtained on Varian Unity Inova 400 (Varian), LC-MS on Waters Acquity UPLC with Waters MICROMASS detector (Waters).

Hydrogel Preparation:

The supramolecular hydrogels (e.g., fMLF and fMLF-derived hydrogelators 1, 2, 3 and 4) were prepared by adding the determined amount of peptides into the DPBS buffer (pH=7.4, Life Technologies), except that the hydrogels for rheology test and controlled release experiment were all prepared in PBS buffer (pH=8.0). The vial contained peptides and the buffer was heated to 100° C. for 1 min to completely dissolve the peptides and the vial was left at room temperature for hydrogel formation. (The stability of the formyl-derived peptides was demonstrated by no change of LC-MS after boiling for 30 mins (see Fig. S16 A-D of Chiu et al., Nature, 501, 52-57 (2013)). And minimum gelation concentration was determined by changing the concentration every 0.025 w/v %.

Transmission Electron Microscopy (TEM):

TEM micrographs were obtained using negatively stained samples on a Morgagni 268 electron microscope (FEI) with a 1 k CCD camera (GATAN). The detailed negative staining procedure is available in the methods of Gao et al., Nat. Commun., 3, 1033 (2012), which is hereby incorporated by reference in its entirety.

Rheology Test:

It was carried out on TA ARES-G2 with the parallel plate (diameter=25 mm) (TA Instruments). The hydrogelators of 1, 2, 3 and 4 were prepared in PBS buffer (pH=8) at their minimum gelation concentrations.

Proteolytic Stability Assay:

It was carried out in 3.5 mL HEPES buffer solution of 1.4 mg (0.4 mg/mL) by adding 2.8 µL of proteinase K solution (>0.8 U/µL, P4850, Sigma) in 37° C. water bath. At the indicated time points, 100 µL was obtained from the digestion soup and quenched by adding 10 µL 1M HCl solution and 90 µL acetonitrile. And 25 µL were injected into the analytic HPLC (the same HPLC system for compound purification) for quantification.

Release Experiment:

The 0.6 mL hydrogels (0.4% w/v) of were formed in in PBS buffer (pH=8). The hydrogel was immersed into 0.6 mL DPBS buffer (pH=7.4, Life Technologies) and it was in 37° C. water bath. Every 2 hours the buffer was changed and the release amount was quantified by analytic HPLC.

Purification of Murine Neutrophils:

Murine bone-marrow derived neutrophils were purified from the bone marrow of the wild type C57BL/6 mice by the EasySep® mouse neutrophil enrichment kit (STEMCELL Technologies). The exact instructions from the kit were followed.

Purification of Human Neutrophils:

Human primary neutrophils were isolated from discarded white blood cell filters (WBF2 filter; Pall Corporation) of healthy donors and were provided by blood bank at the Children's Hospital Boston. The gradient separation method is a standard protocol and has been described in details (see Zhu et al., Proc. Natl. Acad. Sci. USA, 103, 14836-14841 (2006), which is hereby incorporated by reference in its entirety).

Neutrophil Chemotaxis Assay:

The chemotaxis assay and the analysis have been previously described in details (see Sakai et al., Immunity, 37, 1037-1049 (2012)). The chemotaxis assay was carried out on the EZ-Taxiscan (Effector Cell Institute, Tokyo, Japan). Purified neutrophils (1 µL, $3\times10^6$/mL) were added to the lower reservoir of the chamber and 1 µL of the chemoattractant was added to the upper reservoir, with the final concentrations as indicated hereinbelow. Neutrophil migration (at 37° C.) in each of the channels was recorded sequentially every 30 secs for 20 mins. The analysis of the recorded sequential images using DIAS imaging software (Solltech) provided the traces of the migrating neutrophils. Migration speed, directionality and upward directionality were calculated from the (x, y) coordinates derived from the traces. The minimum effective concentrations were determined by 10-fold dilutions.

Neutrophils Reactive Oxygen Species (ROS) Production Assay:

A detailed description of the assay is described in Prasad et al., Nat. Immunol., 12, 752-760 (2011), which is hereby incorporated by reference in its entirety. Briefly, mouse or human neutrophils (at $0.4\times10^6$) were suspended in HBSS containing 4 U/ml HRP, 5.5 µM isoluminol, and 0.2% BSA in a total volume of 180 µL were transferred to the plates. After adding the indicated amount of peptides in 20 µL, the recording of the chemiluminescence starts on a TriStar LB941 microplate luminometer (Berthold Technologies USA).

Mouse Peritonitis Model:

It was described previously in details except that the gel or solution of formyl-peptides were used instead of E. coli (see Sakai et al., Immunity, 37, 1037-1049 (2012), which is hereby incorporated by reference in its entirety). Peritonitis was induced by intraperitoneally injecting the indicated amount of hydrogel or solution into wild type C57BL/6 mice. At the indicated time points, mice were sacrificed and peritoneal exudates were harvested in 3 successive washes with 3 mL of DPBS buffer containing 5 mM EDTA. The cells in the lavage were collected and stained by APC-Gr-1

(APC: Allophycocyanin; eBioscience) and PE-CD11b antibodies (PE: Phycoerythrin; eBioscience) and analyzed by FACS Canto II flow cytometer and FACSDiva software (BD Biosciences).

Example 1—In Vitro and In Vivo Neutrophil Chemotaxis

To demonstrate the concept illustrated in FIG. 1, several fMLF-derived molecules were designed, synthesized and evaluated, namely: hydrogelators 1, 2, 3 and 4. The role of hydrogelator 3 (N-formyl-L-methionyl-L-leucyl-L-3-(2-naphthyl)-alaninyl-D-3-(2-naphthyl)-alanine or fMet-Leu-(2-Nal)-(D-2-Nal) is shown in FIG. 1.

In FIG. 1. In vitro assay: hydrogelator 3 induces chemotaxis of murine and human neutrophils at the minimum effective concentrations of 1.13 μM and 11.3 nM, respectively. In vivo assay: the hydrogelator 3 slowly releases 3 for attracting neutrophils to the location of the hydrogel (at the dosage of 0.935 μmole per mouse). Denotation: f=formyl, M=L-methionyl residue, L=L-leucyl residue, F=L-phenylalaninyl residue, 2-Nal=L-3-(2-naphthyl)-alaninyl residue and D-2-Nal=D-3-(2-naphthyl)-alaninyl residue.

In addition to behaving as a hydrogelator, hydrogelator 3 exhibits three advantageous features: (1) ability to form a hydrogel efficiently (minimum gelation concentration (MGC)=0.125% w/v in DPBS buffer); (2) enhanced stability against proteolysis; and (3) preserved activity to both mouse and human neutrophils. Moreover, hydrogelator 3, in the murine peritonitis model, stimulated a much longer-lasting pro-inflammatory phase than fMLF solution does, and exhibited a two orders of magnitude increase in neutrophil accumulation compared with that of fMLF solution. This work, for the first time may offer a facile approach to convert chemoattractants into hydrogels with exceptional biostability and tailored activity for controlled accumulation of neutrophils in vivo, but validates the concept of the supramolecular hydrogelators acting as chemoattractants for homing cells in a sustainable manner. Besides being a useful tool to study the biology of innate immunity, this prolonged inflammation model may hold promises for various potential therapeutic applications (Dufton et al., *Pharmacol. Ther.*, 127, 175-188 (2010); Gavins, *Trends Pharmacol. Sci.* 31, 266-276 (2010), each of which is hereby incorporated by reference in its entirety), e.g., inhibiting tumor growth (Zhang et al., *Lab. Invest.*, 76, 579-590 (1997); Pachynski et al., *J. Exp. Med.*, 209, 1427-1435 (2012), which is hereby incorporated by reference in its entirety) and may act as a basis for vaccine adjuvants (Kurosaka et al., *J. Immunol.*, 174, 6257-6265 (2005), which is hereby incorporated by reference in its entirety).

Figure 2:
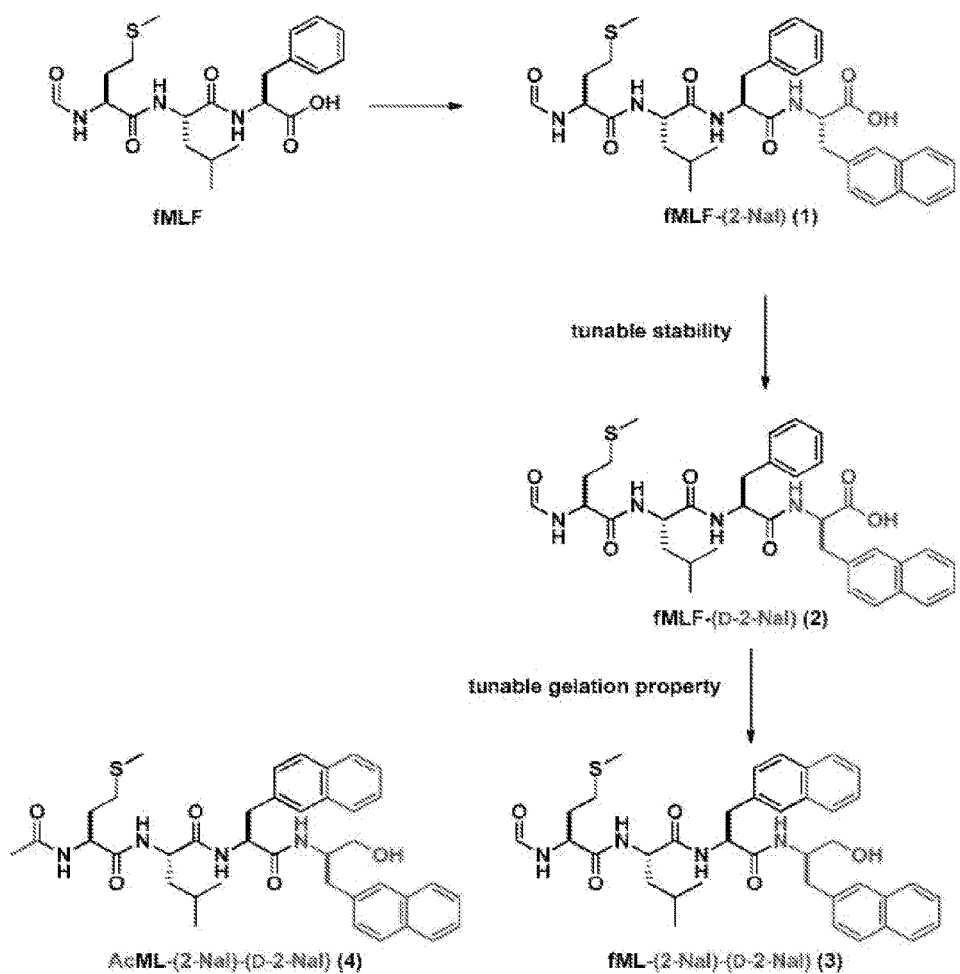
FIG. 2 shows the chemical structures of f-MLF-based hydrogelators 1, 2, 3 and 4 (negative control, Acylated hydrogelator).

The chemical structures of fMLF-derived hydrogelators (hydrogelators 1, 2, 3) and a control peptide (hydrogelator 4) are depicted in FIG. 2.

Example 2—In Vitro Characterization of Hydrogels

Figure 3:
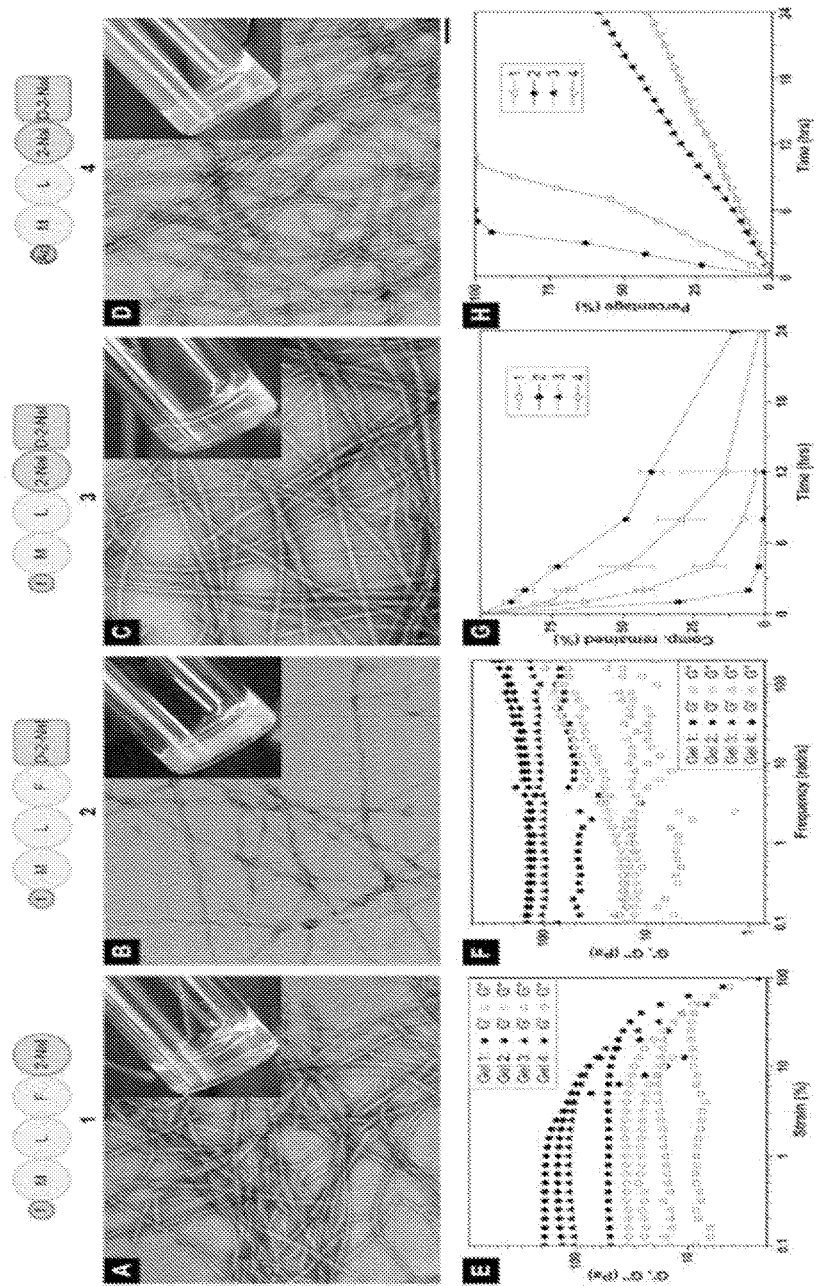
FIGS. 3A-H illustrate characterization of f-MLF-based hydrogelators 1, 2, 3 and 4 (negative control).

FIG. 3 is a characterization of fMLF-derived hydrogelators (hydrogelators 1, 2, 3) and a control peptide (hydrogelator 4) and the hydrogels.

FIGS. 3A-D: The typical TEM images of negatively-stained fibrils of (A) the hydrogelators of 1 (0.20 w/v %), (B) 2 (0.40 w/v %), (C) 3 (0.125 w/v %), and (D) 4 (0.075 w/v %), respectively, with the molecular representation on top (all hydrogels are at pH=7.4 in DPBS buffer; the scale bar is 100 nm; denotation: Ac=acetyl; inset: the optical images of the hydro-gels). (E) Strain sweep and (F) frequency sweep of the hydrogels with the same concentrations as the hydrogels prepared for optical images and TEM. (G) The digestions of hydrogelators 1, 2 and 3, respectively, in 3.5 mL HEPES buffer solution of 1.4 mg (0.4 mg/mL) by adding 2.8 μL of proteinase K solution at 37° C. (H) The self-release profiles of the chemoattractants from the hydrogelators of 1, 2, and 3 (0.4 w/v %) and the control from the hydrogelator 4, respectively, at 37° C.

FIG. 3 also shows the schematic representation of the fMLF-derived peptides that self-assemble in water and form hydrogels and their characterizations (e.g., TEM, rheological properties, proteolytic stability, and the self-release profiles). Based on the structure of fMLF, fMLF was modified at the C-terminus (Sklar et al., *Biochemistry*, 29, 313-316 (1990); Freer et al., *Biochemistry*, 21, 257-263 (1982), each of which is hereby incorporated by reference in its entirety). Since naphthyl group promotes small peptides to form hydrogels (Cherif-Cheikh et al., *Proc. Int. Symp. Control. Rel. Bioact. Mater.*, 25, 798-799 (1998); Maji et al., *PLoS Biol.*, 6, e17 (2008), each of which is hereby incorporated by reference in its entirety), a unnatural amino acid with naphthyl group (2-Nal) was connected to fMLF to obtain fMLF-(2-Nal) (hydrogelator 1). Hydrogelator 1 self-assembles in Dulbecco's Phosphate-Buffered Saline (DPBS) buffer to form a supramolecular hydrogel at concentration of 0.2 w/v % (FIG. 3A, inset). Transmission electron microscopy (TEM) reveals the network of nanofibrils (around 16 nm in diameters) (FIG. 3A) in the hydrogelator 1 (0.2 w/v %), which shows the storage modulus (G') of around 50 Pa and the critical strain of about 10.0% (FIGS. 3E and 3F). As shown in FIG. 3G, being incubated with a powerful protease (e.g., proteinase K), more than 90% of hydrogelator 1 undergoes hydrolysis in the first 2 hr. The self-release of hydrogelator 1 from its hydrogel finishes in about 8 hr. (FIG. 3H).

To improve the stability of the hydrogelators against proteolytic enzymes, the 4th L-amino acid residue was replaced to the corresponding D-amino acid residue (Powell et al., *Pharm. Res.*, 10, 1268-1273 (1993), which is hereby incorporated by reference in its entirety) to obtain a new peptide, fMLF-(2-Nal$_D$) (hydrogelator 2), which still forms a hydrogel (FIG. 3B, inset) but at a higher concentration (MGC: 0.4 w/v %) than that of hydrogelator 1. As shown in the TEM images, the nanofibrils in hydrogelator 2 have diameters around 22 nm (FIG. 3B). Rheology measurement shows the storage modulus and the critical strain of hydrogelator 2 to be around 200 Pa and about 1.0%, respectively (FIGS. 3E and 3F). The incorporation of a D-amino acid, indeed, substantially enhances proteolytic stability of hydrogelator 2 in comparison with that of hydrogelator 1. For example, in the presence of proteinase K, more than 80% and 40% of hydrogelator 2 remains after 2 hr. and after 12 hr., respectively (FIG. 3G). Hydrogelator 2 collapses within the first 4 hr. and completely dissolves after 6 hr. in DPBS buffer at 37° C. (FIG. 3H), suggesting the relatively loose molecular packing in the hydrogelator 2.

Therefore, to obtain the fMLF derivative that has better gelation property, the 3rd amino acid residue on hydrogelator 2 was changed from Phe to 2-Nal, which gave the peptide fML-(2-Nal)-(D-2-Nal) (hydrogelator 3). This simple change boosts intermolecular aromatic-aromatic interaction that promotes molecular self-assembly in water for hydrogelation, so hydrogelator 3 exhibits excellent gelation property with a MGC of 0.125 w/v % (FIG. 3C, inset). The hydrogel prepared at the concentration of 0.125 w/v % has nanofibrils with diameters around 18 nm (FIG. 3C), storage modulus around 100 Pa, and critical strain around 2.0% (FIGS. 3E and 3F). Hydrogelator 3 not only maintains the resistance to the proteinase K proteolysis (FIG. 3G), but the improved gelation property also results in a longer sustained release of hydrogelator 3 in vitro. Hydrogelator 3 releases about 60% of 3 after 24 hr. incubation at 37° C. (FIG. 3H).

The importance of the formyl group for the activities of the N-formyl peptides has been well documented and the replacement of formyl group by acetyl group in fMLF causes a 1000 to 10000 fold activity drop (Marasco et al., *J. Immunol.*, 128, 956-962 (1982); Freer et al., *Biochemistry*, 19, 2404-2410 (1980), each of which is hereby incorporated by reference in its entirety). Therefore, a control molecule of hydrogelator 3, AcML-(2-Nal)-(D-2-Nal) (hydrogelator 4) was synthesized. It forms hydrogel (FIG. 3D, inset) at a low concentration (MGC=0.075 w/v %). Hydrogelator 4 contains nanofibrils with diameters of around 17 nm (FIG. 3D), and has a storage modulus around 140 Pa and a critical strain around 2.0% (FIGS. 3E and 3F). Hydrogelator 4 is less stable against proteolytic digestion by proteinase K than hydrogelator 3. Matching with its excellent gelation property, the hydrogelator 4 also gradually releases hydrogelator 4 (with 40% release at the first 24 hr.) (FIG. 3H).

These four hydrogels, prepared at the MGCs of the hydrogelators, exhibit comparable storage moduli (G'), loss moduli (G"), and critical strains (FIGS. 3E, 3F). Together with that the moduli of these hydrogels depend little on the frequency and the nanofibrils that serve as the matrices of the hydrogels have close diameters (16-22 nm), these results suggest the hydrogels of fMLF-based molecules share similar morphological and rheological properties. In addition, the MGC values of the hydrogelators correlate well with the release profiles of the hydrogelators. For example, the order of the hydrogelators having MGCs from high to low is hydrogelators 2, 1, 3 and 4, which is the same as the order of the rates of the self-release of the hydrogelators from the hydrogels (FIG. 3H). This trend suggests that molecular engineering of the hydrogelators to control the MGC values should be effective and useful for tailoring the release profiles of the chemoattractants.

Figure 4:
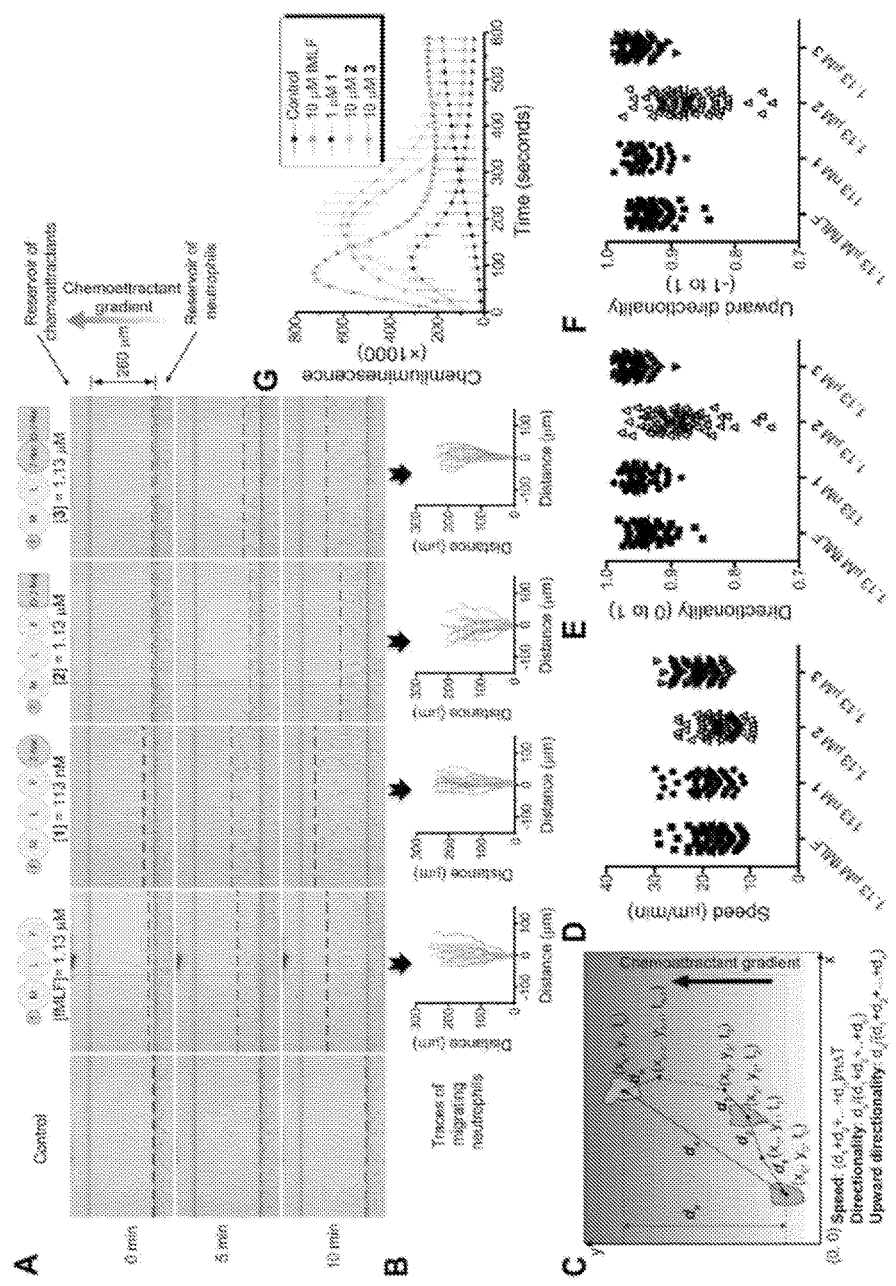
FIGS. 4A-G show the induction of chemotaxis and reactive oxygen species (ROS) production of murine neutrophils by f-MLF-based hydrogelators 1, 2, and 3 in vitro.

Example 3—In Vitro Induction of Murine Neutrophils Chemotaxis and ROS Production FIG. 4 illustrates induction of chemotaxis and ROS production of murine neutrophils by fMLF-derived hydrogelators (1, 2 and 3) in vitro. FIG. 4A shows snapshots of chemotaxis of wild type murine neutrophils at 0, 5 and 10 minutes induced by the gradient of fMLF, hydrogelators 1, 2 and 3 performed on EZ-TAXIScan (Kanegasaki et al., *J. Immunol. Methods*, 282, 1-11 (2003), which is hereby incorporated by reference in its entirety) with the blank control. FIG. 4B shows traces of 20 typical migrating neutrophils corresponding to different chemoattractants in the first 20 minutes. FIG. 4C provides the scheme and formulas for the calculation of the migration parameters. FIGS. 4D-F shows the migration speed (4D), directionality (4E), and upward directionality (4F) of the murine neutrophils during chemotaxis from three independent samples, and each sample has 20 cell traces. FIG. 4G shows ROS production in the neutrophils ($5 \times 10^5$) after stimulation with DMSO (0.1 v/v %, as the negative control), fMLF (10 μM), hydrogelator 1 (1 μM), hydrogelator 2 (10 μM), and hydrogelator 3 (10 μM).

After confirming that the fMLF derivatives act as hydrogelators and exhibit proteolytic stability, the activities of hydrogelators 1-4 to murine neutrophils were determined by measuring chemotaxis and ROS production. FIG. 4A shows the frames of the chemotaxis (performed on the EZ-TAXIScan (Kanegasaki et al., *J. Immunol. Methods*, 282, 1-11 (2003)) induced by different molecules at 0, 5 and 10 min to determine the minimum effective concentrations of the fMLF derivatives. The recorded frames of the first 20 minutes serve as the traces of cell migration (FIG. 4B), which, being analyzed by the algorithm shown in FIG. 4C, provide three important parameters for neutrophil chemotaxis: migration speed (FIG. 4D), directionality (0 to 1) (FIG. 4E), and upward directionality (−1 to 1) (FIG. 4F) to characterize, respectively, how fast the neutrophils move, how straight they migrate, and how faithfully they follow the gradients of the chemoattractants. Chemoattractants will also induce the production of reactive oxygen species (ROS) by the NADPH oxidase assembled on the plasma membrane and phagosome (Kolaczkowska et al., *Nat. Rev. Immunol.*, 13, 159-175 (2013), which is hereby incorporated by reference in its entirety). Thereby, the quantification of ROS production using isoluminol also indicates the activities of the chemoattractants. According to the FIGS. 4A-G, at its minimum effective concentration (1.13 μM), hydrogelator 3 not only induces the chemotaxis of murine neutrophils as effectively as fMLF (i.e., the almost identical migration speed (FIG. 4D) and directionality (FIG. 4E), and slightly better upward directionality (FIG. 4F)), but also exhibits slightly more potent activity for generation of ROS than that of fMLF (FIG. 4G). Interestingly, hydrogelator 1, at 113 nM, exhibits similar chemotactic activities as that of fMLF at 1.13 μM (FIG. 4A), but generates only half as much ROS as fMLF (FIG. 4G). Hydrogelator 2 exhibits drops in the chemotactic activity and the ROS production when compared with fMLF, which matches the previously reported results that the D enantiomer is a less active chemoattractant than the L enantiomer (Vyas et al., *J. Immunol.*, 149, 3605-3611 (1992); Aswanikumar et al., *Biochem. Biophys. Res. Commun.*, 80, 464-471 (1978), each of which is hereby incorporated by reference in its entirety).

Figure 5:
FIG. 5 shows snapshots of wild-type murine neutrophils at 0, 5, 10, and 20 minutes in the gradient of hydrogelator 4 (negative control) starting at 113 μM performed on EZ-TAXIS can.

Hydrogelator 4 failed to induced the chemotaxis even at 113 μM, a 100 fold of the minimum effective concentration of 3 (FIG. 5), which matches the 1000 to 10000 fold activity drop reported in the literature. (Marasco et al., *J. Immunol.*, 128, 956-962 (1982); Freer et al., *Biochemistry*, 19, 2404-2410 (1980), each of which is hereby incorporated by reference in its entirety). Therefore, hydrogelator 4 is considered as having no chemotactic activity, and hydrogelator 4 can be used as a control for hydrogelator 3.

Example 4—In Vitro Induction of Human Neutrophils Chemotaxis and ROS Production

FIG. 6 shows the induction of chemotaxis and ROS production of human neutrophils by hydrogelator 3 in vitro. FIG. 6A shows the snapshots of chemotaxis of purified neutrophils from healthy human donors at 0, 5 and 10 minutes induced by fMLF, hydrogelator 3, and PBS (as the control) performed on EZ-TAXIScan. FIG. 6B shows traces of 20 typical migrating neutrophils corresponding to different chemoattractants. FIGS. 6C-6E show the migration speed (6C), directionality (6D) and upward directionality (6E) of the human neutrophils during chemotaxis from three independent samples, and each sample has 20 cell migration traces. FIG. 6F shows ROS production in the neutrophils ($5 \times 10^5$) after the addition of fMLF (100 nM), hydrogelator 3 (100 nM), and PBS (as the blank control).

The above results clearly show that hydrogelator 3 fulfils all three criteria of the molecular design: excellent gelation property for the purpose of sustained self-release, fair stability against proteolysis, and well preserved chemotactic activity to murine neutrophils. Encouraged by the in vitro activity of hydrogelator 3 to attract murine neutrophils, the activity of hydrogelator 3 on human neutrophils was also investigated. As shown in FIG. 6A, the minimum effective concentration of fMLF to human neutrophils is 11.3 nM determined by a ten-fold serial dilution, which is 100 times lower than the minimum effective concentration of fMLF to murine neutrophils (1.13 µM). This result agrees with the observation that fMLF's activity to murine formyl peptide receptors (FPR) is 100-10,000-fold less than to human and rabbit FPRs (Gao et al., *Nat. Commun.*, 3, 1033 (2012), which is hereby incorporated by reference in its entirety). Moreover, hydrogelator 3, at 11.3 nM, exhibits the same effectiveness as fMLF to human neutrophils, as evidenced by the indistinguishable migration traces (FIG. 6B), similar migration parameters (FIGS. 6C, 6D and 6E), and essentially identical ROS production (FIG. 6F). Although the binding pockets of the mouse and human FPRs might be quite different, which is suggested by fMLF's significantly different activities to FPRs (Gao et al., *Nat. Commun.*, 3, 1033 (2012), which is hereby incorporated by reference in its entirety), the well preserved chemotactic activity of hydrogelator 3 to both mouse and human neutrophils indicates that hydrogelator 3 maintains the binding to both human and murine FPRs. How the modification can satisfy the binding to the two seemingly quite different pockets is surprisingly interesting and certainly deserves further exploration.

Example 5—In Vivo Induction of Murine Neutrophils Chemotaxis and Accumulation at Site of Hydrogel Administration FIG. 7 shows how hydrogels stimulate prolonged accumulation of murine neutrophils in vivo. FIG. 7A shows representative flow cytometry plots showing the neutrophils (Gr1$^+$CD11b$^+$) and the macrophages (Gr1$^-$CD11b$^+$) from the cells collected from the peritoneal lavage of wild-type mice 24 hr after receiving the intraperitoneal injections (IP injections) of 500 µL of PBS (as the control), the solution of fMLF and the hydrogelators of 1, 3 and 4 containing 0.935 µmole of peptides. FIG. 7B shows the number of neutrophils and FIG. 7C shows the ratio of the number of neutrophils vs. the number of macrophages according to the FACS quantification from three independent experiments.

After successfully demonstrating the in vitro properties (i.e., gelation property for sustained release, stability, and the chemotactic activity to both mouse and human neutrophils) of hydrogelator 3, an in vivo murine model was used to determine whether hydrogelator 3 achieves a longer proinflammatory effect for attracting neutrophils than the solution of fMLF. Peritoneal lavages were collected for flow cytometry 24 hr after the injection of DPBS solution, fMLF solution, and hydrogelators of 1, 3, and 4 into mice, respectively. In the representative flow cytometry plots (see FIG. 7A) using the markers Gr1 and CD11b, the double positive (Gr1$^+$CD11b$^+$) corresponds to neutrophils and the Gr1$^-$CD11b$^+$ are macrophages. The acute inflammation started with the rapid influx of neutrophils and switches to monocyte-derived inflammatory macrophages, both from the blood. Although there's not clear cut, the initial influx with a high percentage of neutrophils was considered as pro-inflammatory phase and the later stage with dominant macrophages was the resolution phase. Therefore, the ratio of neutrophils to macrophages was the indicator of the phase of inflammation (Nathan, *Nature*, 420, 846-852 (2002), which is hereby incorporated by reference in its entirety). As shown in FIG. 7A, while the effect of the solution of fMLF almost disappears 24 hr after the injection, hydrogelator 3, having the same amount of N-formyl peptides as the fMLF solution, still attracted high counts of neutrophils. According to the quantification (FIG. 7B), the neutrophil number attracted by hydrogelator 3 was two orders of magnitude higher than that of the solution of fMLF. Moreover, the ratio of the number of neutrophils vs the number of macrophages (FIG. 7C) suggested that the inflammation of peritoneum (peritonitis) induced by hydrogelator 3 was in a much earlier phase than the solution of fMLF, which was in the resolution phase of the inflammation. Although hydrogelator 4 also resulted in stronger accumulation of neutrophils than the solution of fMLF, the total number of neutrophils was still one order of magnitude lower than that induced by hydrogelator 3 (FIG. 7B). In addition, the ratio of neutrophils to macrophages (FIG. 7C) clearly showed that the inflammation induced by hydrogelator 4 is also close to the resolution phase. These results agreed with the chemotactic activities of the hydrogelators 3 and 4, and suggested that the accumulation of neutrophils caused by the hydrogelator 4 was probably due to the inflammatory response toward stable foreign materials.

As the other control, the hydrogelator 1 resulted in similar results as the solution of fMLF: low total number of neutrophils and low ratio of neutrophils to macrophages 24 hr after the injections (FIGS. 7B and 7C). Although hydrogelator 1 is roughly 10 times more chemotactically active as hydrogelator 3 (FIG. 2), the hydrogel of 1 self-release faster than hydrogelator 3, and hydrogelator 1 is less stable than hydrogelator 3. Therefore, the stronger accumulation of neutrophils induced by hydrogelator 3 than by the hydrogelator 1 likely was not only due to the inflammatory response to stable foreign materials (as the case of hydrogelator 4), but also originated from the sustained self-release of more stable chemoattractive hydrogelators. This result suggests that it is feasible to modulate inflammation by controlling the rheological properties of the hydrogels, the self-release profiles, and the stabilities of the hydrogelators.

Because neutrophils, as short-lived cells (Kolaczkowska et al., *Nat. Rev. Immunol.*, 13, 159-175 (2013), which is hereby incorporated by reference in its entirety) have a half-life of 1.5 hr. in the circulation in mice, the accumulation of neutrophils in this murine model is different from the other cell accumulations where the attracted cells remain alive. Therefore, the results, shown in FIG. 7, could not be interpreted as the explosive accumulation of neutrophils induced at first couple of hr all at once and then no activity follows. Instead, the results from 24 hr strongly support that the accumulation of neutrophils was due to a constant attraction by the sustained self-release of the hydrogelators from hydrogelator 3.

Forty-eight hours after injection, (see FIG. 8), the number of neutrophils attracted by hydrogelator 3 is $1.1 \pm 0.3 \times 10^4$ and the ratio of neutrophils to macrophages is $0.05 \pm 0.03$, which showed that the peritonitis induced by the hydrogelator 3 also moved into the resolution phase, suggesting that the controlled release exhausted between 24 hr. and 48 hr. This might be related to the watery environment of peritoneum due to peritoneal fluid.

Discussion of Examples 1-5

In summary, these Examples illustrate the evolution of multifunctional molecular hydrogelators for attracting neutrophils in vitro and in vivo. As the new class of "self-delivery" biomaterials, supramolecular hydrogels are only at its infancy for immunomodulation, with some initial but exciting explorations on vaccines for adaptive immunity (Rudra et al., *Proc. Natl. Acad. Sci. USA*, 107, 622-627 (2010), which is hereby incorporated by reference in its entirety). This disclosed invention is the first example of using molecular self-assembly for the construction of immunomodulatory materials for innate immunity. The self-assembled hydrogelators of fMLF-derived peptides and other formyl receptor modulator peptides, as a unique tool, can be very useful to researchers that need to induce sustained innate immune recruitment, which was unavailable before. Furthermore, the hydrogelators, as described herein, also hold therapeutic potentials that have yet to be explored. More broadly, besides fMLF, there are many small biological peptides, playing essential roles in diverse biological functions. The concept illustrated in this work along with other work has the potential to modify those peptides to form supramolecular hydrogel without compromising the bioactivities. The general concept of using supramolecular hydrogel of bioactive small molecules as "self-delivery" system, thus, provides a novel approach to therapeutics and an attractive and validated alternative to the traditional drug delivery system.

Example 6—Formation of Additional Self-Assembling Peptides

Besides modifying N-formyl-L-methionyl-L-leucyl-L-phenylalanine (fMLF) at the C-terminal end for formation of supramolecular nanofibrils and hydrogels, chemical modification can also be accomplished with other N-formyl peptides (e.g., f-MIVIL, SEQ ID NO: 6, a pentapeptide from *Listeria monocytogenes*), f-MIFL, SEQ ID NO: 7, a tetrapeptide from *Staphylococcus aureus*), f-MFFINILTL, SEQ ID NO: 8, a mitochondrial peptide), f-MFINRWLFS, SEQ ID NO: 9, a mitochondrial peptide), f-AWKYMVD, SEQ ID NO: 10, a synthetic formyl peptide)), peptides having a tert-butyloxycarbonylated (t-Boc) or an acetylated (Ac) N-terminal residue, or a deformylase inhibitor peptide (e.g. GSK1322322). For additional information on these peptides, see Bufe et al., *J. Biol. Chem.*, 287, 33644-33655 (2012); Southgate et al., *J. Immunol.*, 181, 1429-1437 (2008); and U.S. Pat. No. 7,893,056, each of which is hereby incorporated by reference in its entirety.

As an example, GSK1322322, a peptide deformylase (PDF) inhibitor currently being developed for the oral and intravenous treatment of acute bacterial skin and skin structure infections (SSSI) and hospitalized patients with community acquired pneumonia (CAP) (See O'Dwyer et al., *Antimicrob. Agents Chemother.*, 57(3), 2333-2342 (2013), may be chemically modified following the peptide synthesis scheme as illustrated in FIG. 9A to produce a GSK1322322-(2-Nal$_D$) peptide analog-based hydrogelator. The first and second steps of the peptide synthesis can be accomplished according to the methods of Heuisul, P. et al. (*Bioorg. Med. Chem. Lett.*, 18, 2900-2904 (2008) and Kaldor et al., *J. Org. Chem.*, 66, 3495-3501 (2001), respectively. Examples of additional GSK1322322-(2-Nal$_D$) peptide analog-based hydrogelators having an N-terminal deformylase inhibitor component (e.g., GSK1322322) and a 2-Nal$_D$ at the C-terminal are provided in FIG. 9B.

Example 7—Treatment of Sepsis Using CLP Mouse Model

The CLP mouse model for sepsis is described in Kim et al., "The Agonists of Formyl Peptide Receptors Prevent Development of Severe Sepsis after Microbial Infection," *J. Immunol.* 185:4302-4310 (2010), which is hereby incorporated by reference in its entirety. Briefly, for cecal ligation and puncture (CLP), mice will be appropriately anesthetized and a small abdominal midline incision will be made to expose the cecum. The cecum will be ligated below the ileocecal valve, punctured twice through both surfaces (or once for the measurement of cytokine production), using a 22-gauge needle, and the abdomen will be closed. Sham CLP mice will be subjected to the same procedure, but without puncture of the cecum. For the LPS or *Escherichia coli* model, *E. coli* ($1 \times 10^9$ cells/mouse) or 60 mg/kg LPS will be injected i.p., respectively. The test subjects will be administered either (i) fMLF solution 4 times via s.c. injection at 2, 14, 26, and 38 h post-CLP (repeat of the work reported by Kim et al., "The Agonists of Formyl Peptide Receptors Prevent Development of Severe Sepsis after Microbial Infection," *J. Immunol.* 185:4302-4310 (2010), which is hereby incorporated by reference in its entirety); (ii) hydrogelator 3 administered via s.c. injection at 2 h post-CLP, containing the same concentration of fMLF as one of the injections for (i); (iii) hydrogelator 3 administered via s.c. injection at 2 h post-CLP, containing the same concentration of fMLF as two of the injections for (i); and (iv) hydrogelator 3 administered via s.c. injection at 2 h post-CLP, containing the same concentration of fMLF as all four of the injections of (i). Survival will be monitored once daily for 10 days.

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations therefore, is not intended to limit the claimed processes to any order except as may be specified in the claims. Accordingly, the invention is limited only by the following claims and equivalents thereto.

REFERENCES

All publications and patent applications mentioned in this specification are herein incorporated by reference in their entirety to the same extent as if each individual publication or patent application was specifically and individually indicated to be incorporated by reference.

Hubbell et al., Materials engineering for immunomodulation, *Nature*, 462, 449-460 (2009).
Ali et al., Infection-mimicking materials to program dendritic cells in situ, *Nat. Mater.*, 8, 151-158 (2009).
St. John et al., Synthetic mast-cell granules as adjuvants to promote and polarize immunity in lymph nodes, *Nat. Mater.*, 11, 250257 (2012)
DeMuth et al., Polymer multilayer tattooing for enhanced DNA vaccination, *Nat. Mater.*, 12, 367-376 (2013).
Nathan, C., Neutrophils and immunity: challenges and opportunities, *Nat. Rev. Immunol.*, 6, 173-182 (2006).
Mantovani et al., Neutrophils in the activation and regulation of innate and adaptive immunity, *Nat. Rev. Immunol.*, 11, 519-531 (2011).

Ye et al., International Union of Basic and Clinical Pharmacology. LXXIII. Nomenclature for the Formyl Peptide Receptor (FPR) Family, *Pharmacol. Rev.*, 61, 119-161 (2009).

Estroff & Hamilton, Water Gelation by Small Organic Molecules, *Chem. Rev.*, 104, 1201-1218 (2004).

Kolaczkowska & Kubes, Neutrophil recruitment and function in health and inflammation, *Nat. Rev. Immunol.*, 13, 159-175 (2013).

Puga et al., B cell-helper neutrophils stimulate the diversification and production of immunoglobulin in the marginal zone of the spleen, *Nat. Immunol.*, 13, 170-180 (2012).

Gao et al., Impaired Antibacterial Host Defense in Mice Lacking the N-formylpeptide Receptor, *J. Exp. Med.*, 189, 657-662 (1999).

Jagels et al., C5a- and tumor necrosis factor-alpha-induced leukocytosis occurs independently of beta 2 integrins and L-selectin: differential effects on neutrophil adhesion molecule expression in vivo, *Blood*, 85, 2900-2909 (1995).

Rittner et al., Mycobacteria Attenuate Nociceptive Responses by Formyl Peptide Receptor Triggered Opioid Peptide Release from Neutrophils, *PLoS Pathog.*, 5, e1000362 (2009).

Feng et al., Neutrophils Emigrate from Venules by a Transendothelial Cell Pathway in Response to FMLP, *J. Exp. Med.*, 187, 903-915 (1998).

Oda & Katori, Inhibition site of dexamethasone on extravasation of polymorphonuclear leukocytes in the hamster cheek pouch microcirculation, *J. Leukoc. Biol.*, 52, 337-342 (1992).

Colditz & Movat, Kinetics of neutrophil accumulation in acute inflammatory lesions induced by chemotaxins and chemotaxinigens, *J. Immunol.*, 133, 2169-2173 (1984).

Zhang et al., The pattern of monocyte recruitment in tumors is modulated by MCP-1 expression and influences the rate of tumor growth, *Lab. Invest.*, 76, 579-590 (1997).

Pachynski et al., The chemoattractant chemerin suppresses melanoma by recruiting natural killer cell antitumor defenses, *J. Exp. Med.*, 209, 1427-1435 (2012).

Gauthier et al., Differential Contribution of Bacterial N-Formyl-Methionyl-Leucyl-Phenylalanine and Host-Derived CXC Chemokines to Neutrophil Infiltration into Pulmonary Alveoli during Murine Pneumococcal Pneumonia, *Infect. Immun.*, 75, 5361-5367 (2007).

Kress et al., Cell stimulation with optically manipulated microsources, *Nat. Meth.*, 6, 905-909 (2009).

Zhao et al., Directed cell migration via chemoattractants released from degradable microspheres, *Biomaterials*, 26, 5048-5063 (2005).

Maji et al., Functional Amyloids As Natural Storage of Peptide Hormones in Pituitary Secretory Granules, *Science*, 325, 328-332 (2009).

Aida et al., Functional Supramolecular Polymers, *Science*, 335, 813-817 (2012).

Branco et al., Materials from peptide assembly: towards the treatment of cancer and transmittable disease, *Curr. Opin. Chem. Biol.*, 15, 427-434 (2011).

Zhao et al., Molecular hydrogels of therapeutic agents. Chem. Soc. Rev. 38, 883-891 (2009).

Cherif-Cheikh. et al., Autogel™: a new lanreotide prolonged release formulation. Proc. Int. Symp. Control. Rel. Bioact. Mater. 25, 798-799 (1998).

Maji et al., Amyloid as a Depot for the Formulation of Long-Acting Drugs, *PLoS Biol.*, 6, e11 (2008).

Vemula et al., Self-assembled prodrugs: An enzymatically triggered drug-delivery platform, *Biomaterials*, 30, 383-393 (2009).

Dufton & Perretti, Therapeutic anti-inflammatory potential of formyl-peptide receptor agonists, *Pharmacol. Ther.*, 127, 175-188 (2010).

Gavins, Are formyl peptide receptors novel targets for therapeutic intervention in ischaemia-reperfusion injury? *Trends Pharmacol. Sci.*, 31, 266-276 (2010).

Kurosaka et al., Mouse Cathelin-Related Antimicrobial Peptide Chemoattracts Leukocytes Using Formyl Peptide Receptor-Like 1/Mouse Formyl Peptide Receptor-Like 2 as the Receptor and Acts as an Immune Adjuvant, *J. Immunol.*, 174, 6257-6265 (2005).

Sklar et al., Fluorescence analysis of the size of a binding pocket of a peptide receptor at natural abundance, *Biochemistry*, 29, 313-316 (1990).

Freer et al., Formyl peptide chemoattractants: a model of the receptor on rabbit neutrophils, *Biochemistry*, 21, 257-263 (1982).

Powell et al., Peptide Stability in Drug Development. II. Effect of Single Amino Acid Substitution and Glycosylation on Peptide Reactivity in Human Serum, *Pharm. Res.*, 10, 1268-1273 (1993).

Marasco et al., Anti-f Met-Leu-Phe: similarities in fine specificity with the formyl peptide chemotaxis receptor of the neutrophil, *J. Immunol.*, 128, 956-962 (1982).

Freer et al., Further studies on the structural requirements for synthetic peptide chemoattractants, *Biochemistry*, 19, 2404-2410 (1980).

Kanegasaki et al., A novel optical assay system for the quantitative measurement of chemotaxis, *J. Immunol. Methods*, 282, 1-11 (2003).

Vyas et al., Biochemical specificity of H-2M3a. Stereospecificity and space-filling requirements at position 1 maintain N-formyl peptide binding, *J. Immunol.*, 149, 3605-3611 (1992).

Aswanikumar et al., Antibiotics and peptides with agonist and antagonist chemotactic activity, *Biochem. Biophys. Res. Commun.*, 80, 464-471 (1978).

Gao & Murphy, Species and subtype variants of the N-formyl peptide chemotactic receptor reveal multiple important functional domains, *J. Biol. Chem.*, 268, 25395-25401 (1993).

Nathan, Points of control in inflammation, *Nature*, 420, 846-852 (2002).

Rudra et al., A self-assembling peptide acting as an immune adjuvant, *Proc. Natl. Acad. Sci. USA*, 107, 622-627 (2010).

Gao et al., Imaging enzyme-triggered self-assembly of small molecules inside live cells, *Nat. Commun.*, 3, 1033 (2012).

Hill et al., 2,2,2-Trifluoroethyl Formate: A Versatile and Selective Reagent for the Formylation of Alcohols, Amines, and N-Hydroxylamines, *Org. Lett.*, 4, 111-113 (2001).

Chiu et al., Direct activation of sensory neurons by bacteria mediates pain and inflammation, *Nature*, 501, 52-57 (2013))

Zhu et al., Deactivation of phosphatidylinositol 3,4,5-trisphosphate/Akt signaling mediates neutrophil spontaneous death, *Proc. Natl. Acad. Sci. USA*, 103, 14836-14841 (2006).

Sakai et al., Reactive Oxygen Species-Induced Actin Glutathionylation Controls Actin Dynamics in Neutrophils, *Immunity*, 37, 1037-1049 (2012).

Prasad et al., Inositol hexakisphosphate kinase 1 regulates neutrophil function in innate immunity by inhibiting phosphatidylinositol-(3,4,5)-trisphosphate signaling, *Nat. Immunol.*, 12, 752-760 (2011).

Bufe et al., Formyl peptide receptors from immune and vomeronasal system exhibit distinct agonist properties, *J. Biol. Chem.*, 287, 33644-33655 (2012)

Southgate et al., Identification of formyl peptides from *Listeria monocytogenes* and *Staphylococcus aureus* as potent chemoattractants for mouse neutrophils, *J. Immunol.*, 181, 1429-1437 (2008)

U.S. Pat. No. 7,893,056

O'Dwyer et al., Comparative analysis of the antibacterial activity of a novel peptide deformylase inhibitor, GSK1322322, *Antimicrob. Agents Chemother.*, 57(3), 2333-2342 (2013)

Heuisul et al., Synthesis, SAR, and X-ray structure of human BACE-1 inhibitors with cyclic urea derivatives, *Bioorg. Med. Chem. Lett.*, 18, 2900-2904 (2008)

Kaldor et al., Stereocontrolled synthesis of cis-dibenzoquinolizine chlorofumarates: curare-like agents of ultrashort duration, *J. Org. Chem.*, 66(10), 3495-3501 (2001)

What is claimed:

1. A peptide comprising up to 35 amino acids, said amino acids having a formylated or acetylated N-terminal residue and a C-terminal residue selected from the group of 2-Nal or 2-Nal$_D$, wherein the peptide, when introduced into aqueous medium, self-assembles to form a hydrogel.

2. The peptide according to claim 1, wherein the amino acids are all D-amino acids.

3. The peptide according to claim 1, wherein the amino acids are a mixture of L-amino acids and D-amino acids.

4. The peptide according to claim 1, wherein the formylated N-terminal residue is f-Met or f-Ala.

5. The peptide according to claim 1, wherein said C-terminal residue is 2-Nal$_D$.

6. The peptide according to claim 5, wherein said peptide exhibits enhanced resistance to proteinase digestion compared to an identical peptide lacking the C-terminal 2-Nal$_D$ residue.

7. The peptide according to claim 6, wherein said proteinase is proteinase K.

8. The peptide according to claim 1, wherein said peptide is up to 10 amino acids.

9. A peptide having a formylated (f) or acetylated (Ac) N-terminal residue and being selected from the group consisting of f-MLF-(2-Nal) (SEQ ID NO: 1), f-MLF-(2-Nal$_D$), f-ML-(2-Nal)-(2-Nal), f-MIVIL-(2-Nal) (SEQ ID NO: 2), f-MIVIL-(2-Nal$_D$), f-MIFL-(2-Nal) (SEQ ID NO: 3), f-MIFL-(2-Nal$_D$), f-MFINRWLFS-(2-Nal) (SEQ ID NO: 4), f-MFINRWLFS-(2-Nal$_D$), f-MFFINILTL-(2-Nal) (SEQ ID NO: 5), f-MFFINILTL-(2-Nal$_D$), f-AWKYMV$_D$-(2-Nal), f-AWKYMV$_D$-(2-Nal$_D$), f-M$_D$L$_D$F$_D$-(2-Nal$_D$), f-M$_D$L$_D$-(2-Nal$_D$)-(2-Nal$_D$), f-M$_D$I$_D$V$_D$I$_D$L$_D$-(2-Nal$_D$), f-M$_D$I$_D$F$_D$L$_D$-(2-Nal), f-M$_D$F$_D$I$_D$N$_D$R$_D$W$_D$L$_D$F$_D$S$_D$-(2-Nal$_D$), f-M$_D$F$_D$F$_D$I$_D$N$_D$I$_D$L$_D$T$_D$L$_D$-(2-Nal$_D$), f-A$_D$W$_D$K$_D$Y$_D$M$_D$V$_D$-(2-Nal$_D$), Ac-ML-(2-Nal)-(2-Nal$_D$), and Ac-M$_D$L$_D$-(2-Nal)-(2-Nal$_n$).

10. The peptide according to claim 5, wherein said C-terminal 2-Nal$_D$ residue is further connected to a Tn antigen (N-acetylgalactosamine) through a serine residue or at a side chain through a ε-amine of a lysine residue.

11. An immunogenic conjugate comprising an antigenic peptide conjugated to the peptide according to claim 1.

12. The immunogenic conjugate according to claim 11, wherein the antigenic peptide comprises an epitope that induces an antibody mediated immune response.

13. The immunogenic conjugate according to claim 11, wherein the antigenic peptide comprises an epitope that induces a T-cell mediated immune response.

14. A hydrogel composition comprising an aqueous medium and a peptide according to claim 1, wherein the peptide self assembles to form nanofibrils.

15. The hydrogel composition according to claim 14 further comprising an agent selected from the group consisting of an antibiotic agent, a chemotherapeutic agent, an immunotherapeutic agent, and an antigenic agent that comprises an epitope that induces either an antibody mediated or T-cell mediated immune response.

16. A method for eliciting an inflammatory response in a subject comprising:
administering to a subject in need thereof a therapeutically effective amount of the hydrogel composition according to claim 14, wherein said administering is effective to release the peptide from the hydrogel over a period of time and the inflammatory response extends for a duration dependent on the peptide release from the hydrogel.

17. A method for inducing neutrophil accumulation in vivo comprising:
administering to a subject in need thereof a therapeutically effective amount of the hydrogel composition according to claim 14, wherein said administering is effective to release the formyl peptide over a period of time exceeding 12 hours, thereby inducing neutrophil accumulation at the site of administration for a duration dependent on the peptide release from the hydrogel.

18. A method for treating a cancerous condition comprising:
administering to a subject having a cancerous condition a therapeutically effective amount of the hydrogel composition according to claim 14, wherein said administering is effective to inhibit tumor growth or shrink tumor size.

19. A method of treating a bacterial infection comprising:
administering to a patient having a bacterial infection a therapeutically effective amount of the hydrogel composition according to claim 14, wherein said administering is effective to treat the bacterial infection.

20. A method of making a hydrogel composition comprising introducing a peptide according to claim 1 into an aqueous medium, wherein the peptide self-assembles to form nanofibrils.

* * * * *

UNITED STATES PATENT AND TRADEMARK OFFICE
CERTIFICATE OF CORRECTION

PATENT NO.        : 10,232,037 B2
APPLICATION NO.   : 15/115385
DATED             : March 19, 2019
INVENTOR(S)       : Fan Zhao et al.

Page 1 of 1

It is certified that error appears in the above-identified patent and that said Letters Patent is hereby corrected as shown below:

In the Claims

In Claim 9, at Column 39, Line 38, delete "f-ML-(2-Nal)-(2-Nal)" and insert in its place --f-ML-(2-Nal)-(2-Nal$_D$)--.

Signed and Sealed this
Sixteenth Day of July, 2019

Andrei Iancu
*Director of the United States Patent and Trademark Office*

SEQUENCE LISTING

```
<160> NUMBER OF SEQ ID NOS: 10

<210> SEQ ID NO 1
<211> LENGTH: 4
<212> TYPE: PRT
<213> ORGANISM: artificial
<220> FEATURE:
<223> OTHER INFORMATION: formyl peptide receptor agonists
<220> FEATURE:
<221> NAME/KEY: MISC_FEATURE
<222> LOCATION: (4)..(4)
<223> OTHER INFORMATION: X is 3-(2-naphthyl)-alanine

<400> SEQUENCE: 1

Met Leu Phe Xaa
1

<210> SEQ ID NO 2
<211> LENGTH: 6
<212> TYPE: PRT
<213> ORGANISM: artificial
<220> FEATURE:
<223> OTHER INFORMATION: formyl peptide receptor agonists
<220> FEATURE:
<221> NAME/KEY: MISC_FEATURE
<222> LOCATION: (6)..(6)
<223> OTHER INFORMATION: X is 3-(2-naphthyl)-alanine

<400> SEQUENCE: 2

Met Ile Val Ile Leu Xaa
1               5

<210> SEQ ID NO 3
<211> LENGTH: 5
<212> TYPE: PRT
<213> ORGANISM: artificial
<220> FEATURE:
<223> OTHER INFORMATION: formyl peptide receptor agonists
<220> FEATURE:
<221> NAME/KEY: MISC_FEATURE
<222> LOCATION: (5)..(5)
<223> OTHER INFORMATION: X is 3-(2-naphythyl)-alanine

<400> SEQUENCE: 3

Met Ile Phe Leu Xaa
1               5

<210> SEQ ID NO 4
<211> LENGTH: 10
<212> TYPE: PRT
<213> ORGANISM: artificial
<220> FEATURE:
<223> OTHER INFORMATION: formyl peptide receptor agonists
<220> FEATURE:
<221> NAME/KEY: MISC_FEATURE
<222> LOCATION: (10)..(10)
<223> OTHER INFORMATION: X is 3-(2-naphythyl)-alanine
```

```
<400> SEQUENCE: 4

Met Phe Ile Asn Arg Trp Leu Phe Ser Xaa
1               5                   10

<210> SEQ ID NO 5
<211> LENGTH: 10
<212> TYPE: PRT
<213> ORGANISM: artificial
<220> FEATURE:
<223> OTHER INFORMATION: formyl peptide receptor agonists
<220> FEATURE:
<221> NAME/KEY: MISC_FEATURE
<222> LOCATION: (10)..(10)
<223> OTHER INFORMATION: X is 3-(2-naphythyl)-alanine

<400> SEQUENCE: 5

Met Phe Phe Ile Asn Ile Leu Thr Leu Xaa
1               5                   10

<210> SEQ ID NO 6
<211> LENGTH: 5
<212> TYPE: PRT
<213> ORGANISM: artificial
<220> FEATURE:
<223> OTHER INFORMATION: formyl peptide receptor agonists

<400> SEQUENCE: 6

Met Ile Val Ile Leu
1               5

<210> SEQ ID NO 7
<211> LENGTH: 4
<212> TYPE: PRT
<213> ORGANISM: artificial
<220> FEATURE:
<223> OTHER INFORMATION: formyl peptide receptor agonists

<400> SEQUENCE: 7

Met Ile Phe Leu
1

<210> SEQ ID NO 8
<211> LENGTH: 9
<212> TYPE: PRT
<213> ORGANISM: artificial
<220> FEATURE:
<223> OTHER INFORMATION: formyl peptide receptor agonists

<400> SEQUENCE: 8

Met Phe Phe Ile Asn Ile Leu Thr Leu
1               5

<210> SEQ ID NO 9
<211> LENGTH: 9
<212> TYPE: PRT
<213> ORGANISM: artificial
<220> FEATURE:
<223> OTHER INFORMATION: formyl peptide receptor agonists

<400> SEQUENCE: 9

Met Phe Ile Asn Arg Trp Leu Phe Ser
1               5

<210> SEQ ID NO 10
<211> LENGTH: 7
<212> TYPE: PRT
```

```
<213> ORGANISM: artificial
<220> FEATURE:
<223> OTHER INFORMATION: formyl peptide receptor agonists

<400> SEQUENCE: 10

Ala Trp Lys Tyr Met Val Asp
1               5
```